United States Patent [19]

Beaulieu et al.

[11] Patent Number: 5,574,015
[45] Date of Patent: Nov. 12, 1996

[54] ISOSTERIC ANTIHERPES PEPTIDE DERIVATIVES

[75] Inventors: Pierre L. Beaulieu, Montréal; Robert Déziel, Ville Mont-Royal; Neil Moss; Raymond Plante, both of Laval, all of Canada

[73] Assignee: Bio-Mega/Boehringer Ingelheim Research Inc., Laval, Canada

[21] Appl. No.: 324,434

[22] Filed: Oct. 17, 1994

Related U.S. Application Data

[63] Continuation of Ser. No. 25,507, Mar. 3, 1993, abandoned, which is a continuation-in-part of Ser. No. 849,918, Mar. 12, 1992, abandoned.

[51] Int. Cl.$^6$ .................................................. A61K 38/06
[52] U.S. Cl. ........................... 514/18; 514/17; 530/331; 530/330
[58] Field of Search ..................... 514/17, 18; 530/330, 530/331

[56] References Cited

U.S. PATENT DOCUMENTS 4,795,740  1/1989  Cohen ........................ 514/14
4,814,432  3/1989  Freidinger ................. 530/329

*Primary Examiner*—Elizabeth C. Weimar
*Assistant Examiner*—David Lukton
*Attorney, Agent, or Firm*—R. P. Raymond; M-E. M. Devlin; A. R. Stempel

[57] ABSTRACT

Disclosed herein are peptide derivatives of the formula A-B-D-CH$_2$CH{CH$_2$C(O)R$^1$}C(O)-NHCH{CR$^2$(R$^3$)COOH}C(O)-E wherein A is a terminal group, for example an optionally substituted phenylalkanoyl, and B is a N-methyl amino acid residue; or A and B together form a saturated or unsaturated alkylaminocarbonyl; D is an amino acid residue; R$^1$ is alkyl, cycloalkyl, a monosubstituted or a disubstituted amino; R$^2$ is hydrogen or alkyl and R$^3$ is alkyl, or R$^2$ is hydrogen and R$^3$ is phenylalkyl, or R$^2$ and R$^3$ are joined to form a cycloalkyl; and E is a terminal unit, for example, an alkylamino or a monovalent amino acid radical such as NHCH(alkyl)C(O)OH. The derivatives are useful for treating herpes infections.

14 Claims, 1 Drawing Sheet

Fig. 1

ISOSTERIC ANTIHERPES PEPTIDE DERIVATIVES

This is a continuation of application Ser. No. 08/025,507, filed Mar. 3, 1993, now abandoned, which is a continuation-in-part of application Ser. No. 07/849,918, filed Mar. 12, 1992, now abandoned.

FIELD OF INVENTION

This invention relates to peptide derivatives having antiviral properties and to means for using the derivatives to treat viral infections. More specifically, the invention relates to peptide derivatives (hereinafter called "peptides") exhibiting activity against herpes viruses, to pharmaceutical compositions comprising the peptides, and to methods of using the peptides to inhibit the replication of herpes virus and to treat herpes infections.

BACKGROUND OF THE INVENTION

Herpes viruses inflict a wide range of diseases against humans and animals. For instance, herpes simplex viruses, types 1 and 2 (HSV-1 and HSV-2), are responsible for cold sores and genital lesions, respectively; varicella zoster virus (VZV) causes chicken pox and shingles; and the Epstein-Barr virus (EBV) causes infectious mononucleosis.

Over the past two decades, a class of compounds known as the purine and pyrimidine nucleoside analogs has received the most attention by investigators in the search for new therapeutic agents for treatment of herpes virus infections. As a result, several nucleoside analogs have been developed as antiviral agents. The most successful to date is acyclovir which is the agent of choice for treating genital herpes simplex infections.

Nevertheless, in spite of some significant advances, the need for effective, safe therapeutic agents for treating herpes viral infections continues to exist. For a review of current therapeutic agents in this area, see M. C. Bahata, "Antiviral Drugs: Pharmacokinetics, Adverse Effects and Therapeutic Use", J. Pharm. Technol., 3, 100 (1987).

The present application discloses a group of peptide derivatives having activity against herpes viruses. The selective action of these peptides against herpes viruses, combined with a wide margin of safety, renders the peptides as desirable agents for combating herpes infections.

The following references disclose peptides or peptide derivatives which have been associated with antiherpes activity:

B. M. Dutia et al., Nature, 321, 439 (1986),

E. A. Cohen et al., Nature, 321, 441 (1986),

J. H. Subak-Sharpe et al., UK patent application 2185024, published Jul. 8, 1987, P. Gaudreau et al., J. Biol. Chem., 262., 12413 (1987), E. A. Cohen et al., U.S. Pat. No. 4,795,740, Jan. 3, 1989, R. Freidinger et al., U.S. Pat. No. 4,814,432, Mar. 21, 1989

V. M. Garskey et al., U.S. Pat. No. 4,837,304, Jun. 6, 1989

R. Colonno et al., U.S. Pat. No. 4,845,195, Jul. 4, 1989,

P. Gaudreau et al., J. Med. Chem 33, 723 (1990),

J. Adams et al., European patent application 408,973, published Jan. 23, 1991,

P. L. Beaulieu et al., European patent application 411,332, published Feb. 6, 1991, J. Adams et al., European patent application 411,333, published Feb. 6, 1991, J. Adams et al., European patent application 411,334, published Feb. 6, 1991, R. L. Tolman et al., European patent application 412,595, published Feb. 13, 1991, W. T. Ashton et al., European patent application 438,873, published Jul. 31, 1991, P. L. Beaulieu et al., European patent application 461,546, published Dec. 18, 1991, and P. Gaudreau et al., J. Med. Chem., 35, 346 (1992).

The subject peptides of the previous reports can be distinguished from the peptides of the present application by characteristic structural and biological differences.

A noteworthy structural characteristic which distinguishes the present peptides from the usual peptide is that they contain a ketomethylene group in place of an internally located amide group. Hence, the present peptides can be considered to be ketomethylene isosteres.

Abbreviations and symbols used hereinafter are defined in "Details of the Invention" section of this application.

SUMMARY OF THE INVENTION

The peptides of this invention are represented by formula 1

$$\text{A-B-D-CH}_2\text{CH}\{\text{CH}_2\text{C(O)R}^1\}\text{C(O)—NHCH}\{\text{CR}_2(\text{R}^3)\text{COOH}\}\text{C(O)-E} \qquad 1$$

wherein

A is phenyl(lower)alkanoyl; phenyl(lower)alkanoyl monosubstituted on the aromatic portion thereof with a lower alkyl, amino, halo, hydroxy or lower alkoxy; lower alkanoyl disubstituted with phenyl or monosubstituted phenyl wherein the monosubstituent is selected from the group consisting of lower alkyl, halo, hydroxy and lower alkoxy; or {phenyl(lower)alkyl}aminocarbonyl; and B is $N(CH_3)$—$CHR^4C(O)$ wherein $R^4$ is lower alkyl; or A and B taken together form a saturated or unsaturated alkylaminocarbonyl of the formula $R^5$—NH—C(O) wherein $R^5$ is (2–10 C)-alkyl, lower cycloalkyl, 1-(lower alkyl)-(lower cycloalkyl), 1(2-propenyl)-3-butenyl, 1-methyl-1-(2-propenyl)-3-butenyl or 1-ethyl-1-(2-propenyl)-3-butenyl;

D is NH—$CHR^6C(O)$ wherein $R^6$ is lower alkyl or a lower alkyl monosubstituted with carboxy, hydroxy, mercapto or benzyloxy;

$R^1$ is lower alkyl, lower cycloalkyl, 1-(lower alkyl)-(lower cycloalkyl), or $NR^7R^8$ wherein $R^7$ is hydrogen or lower alkyl and $R^8$ is lower alkyl, or $R^7$ and $R^8$ together with the nitrogen atom to which they are attached form a pyrrolidino, piperidino, morpholino or 4-methylpiperazino;

$R^2$ is hydrogen or lower alkyl and $R^3$ is lower alkyl, or $R^2$ is hydrogen and $R^3$ is lower alkenyl or phenyl-(1–4

C)alkyl, or $R^2$ and $R^3$ together with the carbon atom to which they are attached form a lower cycloalkyl; and E is $NHR^9$ wherein $R^9$ is (4–9C)alkyl; lower cycloalkyl; lower cycloalkyl monosubstituted or disubstituted with lower alkyl or (lower alkyl)-(lower cycloalkyl); or E is $NHNR\ R$ wherein $R^{10}R^{11}$ wherein $R^{10}$ is hydrogen or lower alkyl and $R^{11}$ is (4–9C)alkyl; or E is $NHCH(R^{12})$—Z wherein $R^{12}$ is (4–9C)alkyl, lower cycloalkyl or (lower cycloalkyl)-(lower alkyl) and Z is $CH_2OH$, $C(O)OH$, $C(O)NH_2$ or $C(O)OR^{13}$ wherein $R^{13}$ is lower alkyl;

or a therapeutically acceptable salt thereof.

A preferred group of the peptides of this invention is represented by formula 1 wherein A is phenyl(lower)alkanoyl; (4-aminophenyl)-(lower)-alkanoyl; (4-halophenyl)-(lower)alkanoyl; (4-hydroxyphenyl)-(lower)alkanoyl; {4-(lower alkoxy)phenyl}-(lower)alkanoyl; lower alkanoyl disubstituted with phenyl, 4-halophenyl or 4-(lower alkoxy)phenyl; or a phenyl(lower)alkylaminocarbonyl; and B is (N-Me)Val, (N-Me)Ile or (N-Me)Tbg; or A and B together form a saturated or unsaturated alkylaminocarbonyl of the formula $R^5$—NH—C(O) wherein $R^5$ is as defined hereinabove; D is amino acid residue of (S)-2-amino-3-hydroxy-3-methylbutyric acid or (R)-2-amino-3-mercapto-3-methylbutyric acid or an amino acid residue selected from Val, Ile, Tbg and β-EtNva, $R^1$ is lower alkyl, lower cycloalkyl, 1-(lower alkyl)-(lower cycloalkyl), $NMe_2$, $NEt_2$, pyrrolidino or morpholino; $R^2$ and $R^3$ are as defined hereinabove; and E is $NHR^9$ wherein $R^9$ is (4–9C) alkyl; lower cycloalkyl; lower cycloalkyl monosubstituted or disubstituted with lower alkyl; or (lower alkyl)-(lower cycloalkyl); or E is $NHNR^{10}R^{11}$ wherein $R^{10}$ is hydrogen, methyl or ethyl and $R^{11}$ is (4–9C)alkyl; or E is $NHCH(R^{12})$-Z wherein $R^{12}$ is (4–9C)alkyl or (lower cycloalkyl)methyl and Z is as defined hereinabove; or a therapeutically acceptable salt thereof.

A more preferred group of the peptides is represented by formula 1 wherein A is phenylacetyl, phenylpropionyl, (4-aminophenyl)propionyl, (4-fluorophenyl)propionyl, (4-hydroxyphenyl)propionyl, (4-methoxyphenyl)propionyl, 2-(phenylmethyl)-3-phenylpropionyl, 2-{(4-fluorophenyl)methyl}-3-(4-fluorophenyl)propionyl, 2-{(4-methoxyphenyl)methyl}-3-(4-methoxyphenyl)propionyl or benzylaminocarbonyl; B is (N-Me)-Val or (N-Me)-Ile; D is Val, Ile or Tbg; $R^1$ is 1-methylethyl, 1,1-dimethylethyl, 1-methylpropyl, 1,1-dimethylpropyl, 2,2-dimethylpropyl, cyclobutyl, cyclopentyl, cyclohexyl, 1-methylcyclopentyl, $NMe_2$, $NEt_2$, pyrrolidino or morpholino; $R^2$ is hydrogen and $R^3$ is methyl, ethyl, 1-methylethyl, 1,1-dimethylethyl, propyl, 2-propenyl or benzyl, and the carbon atom bearing $R^2$ and $R^3$ has the (R)-configuration, or $R^2$ and $R^3$ each independently is methyl or ethyl, or $R^2$ and $R^3$ together with the carbon atom to which they are attached form a cyclobutyl, cyclopentyl or cyclohexyl; and E is $NHR^9$ wherein $R^9$ is 2-methylpropyl, 2,2-dimethylpropyl, 1(R),2,2-trimethylpropyl, 1,1,2,2-tetramethylpropyl, 1(R)-ethyl-2,2-dimethylpropyl, 2-(R,S)-methylbutyl, 2,2-dimethylbutyl, 3,3-dimethylbutyl, 1(R),2,2-trimethylbutyl, 1(R),3,3-trimethylbutyl, 2-ethylbutyl, 2,2-diethylbutyl, 2-ethyl-1(R)-methylbutyl, 2-ethyl-2-methylbutyl, 1(R)-ethyl-3,3-dimethylbutyl, 2,2-dimethylpentyl, cis- or trans-2-methylcyclohexyl, 2,2-dimethylcyclohexyl or cyclohexylmethyl; or E is $NHNR^{10}R^{11}$ wherein $R^{10}$ is hydrogen, methyl or ethyl and $R^{11}$ is 1,1-dimethylethyl; or E is $NHCH(R^{12})$-Z wherein the carbon atom bearing $R^{12}$ has the (S)-configuration, $R^{12}$ is 1,1-dimethylethyl, 1-methylpropyl, 2-methylpropyl, 2,2-dimethylpropyl or cyclohexylmethyl and Z is $CH_2OH$, $C(O)OH$, $C(O)NH_2$ or $C(O)OR^{13}$ wherein $R^{13}$ is methyl, ethyl or propyl; or a therapeutically acceptable salt thereof.

Another more preferred group of the peptides is represented by formula 1 wherein A and B together form a saturated or unsaturated alkylaminocarbonyl selected from the group of butylaminocarbonyl, 1-methylethylaminocarbonyl, 1-methylpropylaminocarbonyl, 1-ethylpropylaminocarbonyl, 1,1-dimethylbutylaminocarbonyl, 1-ethylbutylaminocarbonyl, 1-propylbutylaminocarbonyl, 1-ethylpentylaminocarbonyl, 1-butylpentylaminocarbonyl, 2-ethylbutylaminocarbonyl, 2-ethylpentylaminocarbonyl, 1-methyl-1-propylbutylaminocarbonyl, 1-ethyl-1-propylbutylaminocarbonyl, 1,1-dipropylbutylaminocarbonyl, (1-propylcyclopentyl)aminocarbonyl, (1-propylcyclohexyl)aminocarbonyl, 1-(2-propenyl)-3-butenylaminocarbonyl, 1-methyl-1-(2-propenyl)-3-butenylaminocarbonyl and 1-ethyl-1-(2-propenyl)-3-butenylaminocarbonyl; and D, $R^1$, $R^2$, $R^3$ and E are as defined in the last instance; or a therapeutically acceptable salt thereof.

A most preferred group of the peptides is represented by formula 1 wherein A is phenylpropionyl, 2-(phenylmethyl)-3-phenylpropionyl or benzylaminocarbonyl; B is (N-Me)Val; D is Tbg; $R^1$ is 1-methylethyl, 1,1-dimethylethyl, 1-methylpropyl, 1,1-dimethylpropyl, 2,2-dimethylpropyl, cyclobutyl, cyclopentyl, cyclohexyl or 1-methylcyclopentyl; $R^2$ is hydrogen and $R^3$ is methyl, ethyl, 1-methylethyl, propyl or benzyl, and the carbon atom bearing $R^2$ and $R^3$ has the (R)-configuration, or $R^2$ and $R^3$ each independently is methyl or ethyl, or $R^2$ and $R^3$ together with the carbon atom to which they are attached form a cyclobutyl, cyclopentyl or cyclohexyl; and E is $NHR^9$ wherein $R^9$ is 2,2-dimethylpropyl, 1(R),2,2-trimethylpropyl, 1(R)-ethyl-2,2-dimethylpropyl, 2,2-dimethylbutyl or 1(R)-ethyl-3,3-dimethylbutyl or E is $NHCH(R^{12})$-Z wherein the carbon atom bearing $R^{12}$ has the (S)-configuration, $R^{12}$ is 2,2-dimethylpropyl and Z is $CH_2OH$, $C(O)OH$, $C(O)NH_2$ or $C(O)OR^{13}$ wherein $R^{13}$ is methyl, ethyl or propyl; or a therapeutically acceptable salt thereof.

Another most preferred group of the peptides is represented by formula 1 wherein A and B together form a saturated or unsaturated alkylaminocarbonyl selected from the group of 1-ethylpropylaminocarbonyl, 1-ethylbutylaminocarbonyl, 1-propylbutylaminocarbonyl, 2-ethylpentylaminocarbonyl, 1-methyl-1-propylbutylaminocarbonyl, 1-ethyl-1-propylaminocarbonyl, 1,1-dipropylbutylaminocarbonyl, (1-propylcyclopentyl)aminocarbonyl, 1-(2-propenyl)-3-butenylaminocarbonyl and 1-ethyl-1-(2-propenyl)-3-butenylaminocarbonyl; and D, $R^1$, $R^2$, $R^3$ and E are as defined in the last instance; or a therapeutically acceptable salt thereof.

Included within the scope of this invention is a pharmaceutical composition comprising an antiherpes virally effective amount of a peptide of formula 1, or a therapeutically acceptable salt thereof, and a pharmaceutically or veterinarily acceptable carrier.

Also included within the scope of this invention is a cosmetic composition comprising a peptide of formula 1, or a therapeutically acceptable salt thereof, and a physiologically acceptable carrier suitable for topical application.

An important aspect of the invention involves a method of treating a herpes viral infection in a mammal by administering to the mammal an antiherpes virally effective amount of the peptide of formula 1, or a therapeutically acceptable salt thereof.

Another important aspect involves a method of inhibiting the replication of herpes virus by contacting the virus with a herpes viral ribonucleotide reductase inhibiting amount of the peptide of formula 1, or a therapeutically acceptable salt thereof.

Still another aspect involves a method of treating a herpes viral infection in a mammal by administering thereto an antiherpes virally effective amount of a combination of the peptide of formula 1, or a therapeutically acceptable salt thereof, and an antiviral nucleoside analog. A pharmaceutical composition comprising the combination is also within the scope of this invention.

Processes for preparing the peptides of formula 1 are described hereinafter.

DETAILS OF THE INVENTION

General

Alternatively, formula 1 can be illustrated as:

The term 'residue' with reference to an amino acid or amino acid derivative means a radical derived from the corresponding α-amino acid by eliminating the hydroxyl of the carboxy group and one hydrogen of the α-amino group.

In general, the abbreviations used herein for designating the amino acids and the protective groups are based on recommendations of the IUPAC-IUB Commision of Biochemical Nomenclature, see European Journal of Biochemistry 138, 9 (1984). For instance, Val, Ile, Asp, and Leu represent the residues of L-valine, L-isoleucine, L-aspartic acid and L-leucine, respectively.

The asymmetric carbon atoms residing in the principal linear axis (i.e. the backbone) of the peptides of formula 1, exclusive of the terminal groups A and Z (of E) but including the carbon atom bearing "$R^{12}$" when E is NHCH($R^{12}$)-Z as defined herein, have an S configuration. Exceptions occur, however, for the carbon atom bearing the $CH_2C(O)R^1$ side chain wherein $R^1$ is lower alkyl, lower cycloalkyl or 1-(lower alkyl)-(lower cycloalkyl), and for the carbon atom bearing a 2-mecaptoalkyl side chain in the instance when $R^6$ of D is the last mentioned side chain. For the latter two exceptions, the carbon atoms have the R configuration.

Asymmetric carbon atoms residing in the side chain of an amino acid or derived amino acid residue, in the terminal group A, and in the terminal group E when E represents $NHR^9$ as defined herein, may have the S or R configuration.

The symbols "Me", "Et", "Pr" and "Bu" represent the alkyl radicals methyl, ethyl, propyl and butyl, respectively.

The symbols "$MeEt_2C$" and "$EtPr_2C$", for example, represent the radicals 1-ethyl-1-methylpropyl and 1-ethyl-1-propylbutyl, respectively.

The symbol "Tbg" represents the amino acid residue of (S)-2-amino-3,3-dimethylbutanoic acid. The symbol "Cpg" represents the amino acid residue of (S)-α-aminocyclopentaneacetic acid. The symbol "γMeLeu" represents the amino acid residue of (S)-2-amino-4,4-dimethylpentanoic acid. The symbol "γMeLeucinol" represents (S)-2-amino-4,4-dimethylpentanol with one hydrogen removed from the α-amino group. The symbol "β-EtNva" represents the amino acid residue of (S)-2-amino-3-ethylpentanoic acid.

Other symbols used herein are: (N-Me)Val for the residue of (S)-3-methyl-2-(methylamino)butanoic acid; (N-Me)Ile for the residue of (S)-3-methyl-2-(methylamino)pentanoic acid; (N-Me)Tbg for the residue of (S)-2-(methylamino)-3,3-dimethyl butanoic acid; Asp(cyBu) for the residue of (S)-α-amino-1-carboxycyclobutaneacetic acid; Asp(cyPn) for the residue of (S)-α-amino-1-carboxycyclopentaneacetic acid; Asp{(R)-Me}for the residue of 3-(R)-methyl-L-aspartic acid (i.e. {S-(R*,S*)}-2-amino-3-methylbutanedioic acid), Asp{(R)-Pr}for the residue of 3-(R)-propyl-L-aspartic acid (i.e. {S-(R*,S*)}-2-amino-3-propylbutanedioic acid), and Asp{(R)-allyl} for the residue of 3-(R)-allyl-L-aspartic acid (i.e. {S-(R*,S*)}-2-amino-3-(2-propenyl)butanedioic acid).

The term "halo" as used herein means a halo radical selected from bromo, chloro, fluoro or iodo.

The term "(2–10C)alkyl" as used herein means straight and branched chain alkyl radicals containing from two to ten carbon atoms and includes ethyl, butyl, 1-methylpropyl, 1-ethylpropyl, 1-propylbutyl, 2-propylpentyl and the like.

The term "(4–9C)alkyl" as used herein means straight and branched chain alkyl radicals containing from four to nine carbon atoms and includes, for example, 1-methylpropyl, 2-methylpropyl, 2,2-dimethylpropyl, 1,2,2-trimethylpropyl, 3,3-dimethylbutyl, 1-ethyl-2,2-dimethylbutyl and 4,4-dimethylpentyl.

The term "lower alkyl" as used herein, either alone or in combination with another radical, means straight chain alkyl radicals containing one to six carbon atoms and branched chain alkyl radicals containing three to six carbon atoms and includes methyl, ethyl, propyl, butyl, hexyl, 1-methylethyl, 1-methylpropyl, 2-methylpropyl and 1,1-dimethylethyl.

The term "1-(lower alkyl)-(lower cycloalkyl)" as used herein means a lower cycloalkyl radical bearing a lower alkyl substituent at position 1; for example, 1-ethylcyclopropyl, 1-propylcyclopentyl and 1-propylcyclohexyl.

The term "lower cycloalkyl" as used herein, either alone or in combination with another radical, means saturated cyclic hydrocarbon radicals containing from three to six carbon atoms and includes cyclopropyl, cyclobutyl, cyclopentyl and cyclohexyl.

The term "lower alkenyl" as used herein means straight chain alkenyl radicals containing two to six carbon atoms and branched chain alkenyl radicals containing three to six carbon atoms and includes vinyl, 1-propenyl, 2-propenyl, 1-methylethenyl, 2-methyl-1-propenyl, 2-methyl-2-propenyl and 2-butenyl.

The term "lower alkoxy" as used herein means straight chain alkoxy radicals containing one to four carbon atoms and branched chain alkoxy radicals containing three to four carbon atoms and includes methoxy, ethoxy, propoxy, 1-methylethoxy, butoxy and 1,1-dimethylethoxy. The latter radical is known commonly as tert-butoxy.

The term "phenyl-(1–4C)alkyl" as used herein means phenylalkyl radicals wherein the alkyl portion thereof is a straight or branched chain alkyl containing from one to four carbon atoms and includes benzyl, 2-phenylethyl, 3-phenylpropyl, 2-methyl-2-phenylethyl {$PhCH(CH_3)CH_2$},1-ethyl-2-phenylethyl {$PhCH_2CH(C_2H_5)$} and the like.

The term "lower alkanoyl" as used herein, either alone or in combination with another radical, means a 1-oxoalkyl radical wherein the 1-oxoalkyl portion thereof is a straight or branched chain 1-oxoalkyl containing from two to six carbon atoms; for example, acetyl, propionyl (1-oxopropyl) and 1-oxo-5-methylhexyl.

The term "pharmaceutically acceptable carrier" or "veterinarily acceptable carrier" as used herein means a nontoxic, generally inert vehicle for the active ingredient which does not adversely affect the ingredient.

The term "physiologically acceptable carrier" as used herein means an acceptable cosmetic vehicle of one or more non-toxic excipients which do not react with or reduce the effectiveness of the active ingredient contained therein.

The term "veterinarily acceptable carrier" as used herein means a physiologically acceptable vehicle for administering drug substances to domestic animals comprising one or more non-toxic pharmaceutically acceptable excipients which do not react with the drug substance or reduce its effectiveness.

The term "effective amount" means a predetermined antiviral amount of the antiviral agent, i.e. an amount of the agent sufficient to be effective against the viral organisms in vivo.

The term "coupling agent" as used herein means an agent capable of effecting the dehydrative coupling of an amino acid or peptide free carboxy group with a free amino group of another amino acid or peptide to form an amide bond between the reactants. Similarly, such agents can effect the coupling of an acid and an alcohol to form corresponding esters. The agents promote or facilitate the dehydrative coupling by activating the carboxy group. Descriptions of such coupling agents and activated groups are included in general text books of peptide chemistry; for instance, E. Schröder and K. L. Lübke, "The Peptides", Vol. 1, Academic Press, New York, N.Y., 1965, pp 2–128, and K. D. Kopple, "Peptides and Amino acids", W. A. Benjamin, Inc., New York, N.Y., 1966, pp 33–51. Examples of coupling agents are diphenylphosphinyl azide, 1,1'-carbonyldiimidazole, dicyclohexylcarbodiimide, N-hydroxysuccinimide, or 1-hydroxybenzotriazole in the presence of dicyclohexylcarbodiimide. A very practical and useful coupling agent is (benzotriazol-1-yloxy)tris-(dimethylamino)-phosphonium hexafluorophosphate, described by B. Castro et al., Tetrahedron Letters, 1219 (1975), see also D. Hudson, J. Org. Chem., 53, 617 (1988), either by itself or in the presence of 1-hydroxybenzotriazole. Still another very practical and useful coupling agent is the commercially available 2-(1H-benzotriazol-1-yl)-N,N, N', N'-tetramethyluronium tetrafluoroborate Process The peptides of formula 1 can be prepared by processes which incorporate therein methods commonly used in peptide synthesis such as the classical solution coupling of amino acid residues and/or peptide fragments. Such methods are described, for example, by E. Schröder and K. Lübke, cited above, in the textbook series, "The Peptides: Analysis, Synthesis, Biology", E. Gross et al., Eds., Academic Press, New York, N.Y., 1979–1987, Volumes 1 to 8, and by J. M. Stewart and J. D. Young in "Solid Phase Peptide Synthesis", 2nd ed., Pierce Chem. Co., Rockford, Ill., USA, 1984.

A common feature of the aforementioned processes for the peptides is the protection of the reactive side chain groups of the various amino acid residues or derived amino acid residues (or, if required, non-peptidic fragments of the peptide) with suitable protective groups which will prevent a chemical reaction from occurring at that site until the protective group is ultimately removed. Also common is the protection of an α-amino group on an amino acid or a fragment while that entity reacts at the carboxy group, followed by the selective removal of the α-amino protective group to allow subsequent reaction to take place at that location. Another common feature is the initial protection of the C-terminal carboxyl of the amino acid residue or peptide fragment, if present, which is to become the C-terminal function of the peptide, with a suitable protective group which will prevent a chemical reaction from occurring at that site until the protective group is removed after the desired sequence of the peptide has been assembled.

A key intermediate for the peptides of formula 1 is the intermediate of formula 2

W-D-CH$_2$CH{CH$_2$C(O)R$^1$}C(O)OH                      2 wherein W is an α-aminoprotective group, e.g. tert-butyloxycarbonyl (Boc), benzyloxycarbonyl (Z) or fluoren-9-ylmethoxycarbonyl (Fmoc), and D and R$^1$ are as defined herein. The compound can be prepared by a Michael addition of an allyl ester of the formula W-D-CH$_2$C(O)OCH$_2$CH=CH$_2$ to a fumaroyl derivative of the formula (lower alkyl)—OC(O)CH=CHC(O)R$^1$ to give the Michael adduct of formula W-D-CH{C(O)OCH$_2$CH=CH$_2$}CH{CH$_2$C(O)R$^1$}C(O)O—(lower alkyl).

Thereafter, treatment of the latter compound with tetrakistriphenylphosphine palladium and triphenylphosphine in the presence of pyrrolidine, according to the method of R. Déziel, Tetrahedron Letters, 28, 4371 (1987), effects hydrolysis and subsequent decarboxylation of the allyl ester to give the corresponding alkyl ester of the key intermediate. Hydrolysis of the latter ester in the presence of a base, e.g. sodium hydroxide or lithium hydroxide, gives the key intermediate as a diastereoisomeric mixture.

Alternatively, the key intermediate of formula 2 wherein W and D are as defined in the last instance and R$^1$ is NR$^7$R$^8$ wherein R$^7$ and R$^8$ each is lower alkyl or R$^7$ and R$^8$ together with the nitrogen atom to which they are attached form a pyrrolidino, piperidino, morpholino or 4-methylpiperazino can be prepared as follows: The previously mentioned allyl ester of formula W-D-CH$_2$C(O)OCH$_2$CH=CH$_2$ wherein W and D are as defined herein is reacted according to the conditions of the Michael reaction with a fumaroyl derivative of formula BzlOC(O)CH=CHC(O)OBzl {(E)-2-butenedioc acid dibenzyl ester} to give the corresponding Michael adduct of formula W-D-(RS)—CH{C(O)OBzl}CH$_2$C(O)OBzl}C(O)—OCH$_2$CH=CH$_2$. Treatment of the latter adduct with tetrakistriphenylphosphine palladium and triphenylphosphine in the presence of pyrrolidine (Déziel, vide supra) gives the corresponding dibenzyl ester of formula W-D-CH$_2$—(R,S)—CH{CH$_2$C(O)OBzl}C(O)OBzl. Subsequent hydrogenolysis in the presence of palladium hydroxide on carbon gives the corresponding dicarboxylic acid which is transformed into the corresponding anhydride by heating with excess acetic anhydride. Reaction of the anhydride with the appropriate secondary amine in the presence of pyridine gives a mixture of regioisomers with a preponderance of the desired isomer of formula W-D-CH$_2$—(RS)—CH{CH$_2$C(O)NR$^7$R$^8$}C(O)—OH in which W,D and NR$^7$R$^8$ are as defined herein. The latter product is converted to its benzyl ester and the resulting mixture of regioisomers is separated by high performance liquid chromatography to give the desired isomer as the preponderant product. Subsequent hydrogenation of the latter product in the presence of palladium hydroxide on carbon yields the key intermediate of formula 2 wherein W and D are as defined herein and R$^1$ is NR$^7$R$^8$ as defined herein.

In general, therefore, a peptide of formula 1 can be prepared by the stepwise coupling, in the order of the sequence of the peptide, of the appropriate amino acid or derived amino acid residues, and non-peptidic fragments of the peptide (such as the key intermediates), which if required are suitably protected, and eliminating all protecting groups, if present, at the completion of the stepwise coupling to obtain the peptide of formula 1. More specific processes are illustrated in the examples hereinafter.

The peptide of formula 1 of this invention can be obtained in the form of a therapeutically acceptable salt. In the instance where a particular peptide has a residue which functions as a base, examples of such salts of the base are those with organic acids, e.g. acetic, lactic, succinic, methanesulfonic or p-toluenesulfonic acid, as well as polymeric acids such as tannic acid or carboxymethyl cellulose, and also salts with inorganic acids such as hydrohalic acids, e.g. hydrochloric acid, or sulfuric acid, or phosphoric acid. If desired, a particular acid addition salt is converted into another acid addition salt, such as a non-toxic, pharmaceutically acceptable salt, by treatment with the appropriate ion exchange resin in the manner described by R. A. Boissonnas et al., Helv. Chim. Acta, 43, 1849 (1960).

In the instance where a particular peptide has one or more free carboxy groups, examples of such salts of the carboxy group are those with the sodium, potassium or calcium cations, or with organic bases, for example, triethylamine or N-methylmorpholine.

Antiherpes Activity

The antiviral activity of the peptides of formula 1 can be demonstrated by biochemical, microbiological and biological procedures showing the inhibitory effect of the compounds on the replication of herpes simplex viruses, types 1 and 2 (HSV-1 and HSV-2), and other herpes viruses, for example, varicella zoster virus (VZV) and Epstein-Barr virus (EBV).

In the examples hereinafter, the inhibitory effect on herpes ribonucleotide reductase is noted for exemplary peptides of formula 1. Noteworthy, in the connection with this specific inhibition of herpes ribonucleotide reductase, is the relatively minimal effect or absence of such an effect of the peptides on cellular ribonucleotide reductase activity required for normal cell replication.

A method for demonstrating the inhibitory effect of the peptides of formula 1 on viral replication is the cell culture technique; see, for example, T. Spector et al., Proc. Natl. Acad. Sci. USA, 82, 4254 (1985).

The therapeutic effect of the peptides can be demonstrated in laboratory animals, for instance, by using an assay based on the murine model of herpes simplex virus-induced ocular disease for antiviral drug testing, described by C. R. Brandt et al., J. Virol. Meth., 36, 209 (1992).

When a peptide of this invention, or one of its therapeutically acceptable salts, is employed as an antiviral agent, it is administered topically or systemically to warm-blooded animals, e.g. humans, pigs or horses, in a vehicle comprising one or more pharmaceutically acceptable carriers, the proportion of which is determined by the solubility and chemical nature of the peptide, chosen route of administration and standard biological practice. For topical administration, the peptide can be formulated in pharmaceutically accepted vehicles containing 0.1 to 5 percent, preferably 0.5 to 2 percent, of the active agent. Such formulations can be in the form of a solution, cream or lotion.

For systemic administration, the peptide of formula 1 is administered by either intravenous, subcutaneous or intramuscular injection, in compositions with pharmaceutically acceptable vehicles or carriers. For administration by injection, it is preferred to use the peptide in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in standard pharmaceutical texts, e.g. in "Remington's Pharmaceutical Sciences", 18th ed, Mack Publishing Company, Easton, Pa., 1990.

The dosage of the peptide will vary with the form of administration and the particular active agent chosen. Furthermore, it will vary with the particular host under treatment. Generally, treatment is initiated with small increments until the optimum effect under the circumstances is reached. In general, the peptide is most desirably administered at a concentration level that will generally afford antivirally effective results without causing any harmful or deleterious side effects.

With reference to topical application, the peptide is administered cutaneously in a suitable topical formulation to the infected area of the body e.g. the skin or part of the oral or genital cavity, in an amount sufficient to cover the infected area. The treatment should be repeated, for example, every four to six hours until lesions heal.

With reference to systemic administration, the peptide of formula 1 is administered at a dosage of 10 µg to 500 µg per kilogram of body weight per day, although the aforementioned variations will occur. However, a dosage level that is in the range of from about 10 µg to 200 µg per kilogram of body weight per day is most desirably employed in order to achieve effective results.

Another aspect of this invention comprises a cosmetic composition comprising a herpes viral prophylactic amount of the peptide of formula 1, or a therapeutically acceptable salt thereof, together with a physiologically acceptable cosmetic carrier. Additional components, for example, skin softeners, may be included in the formulation. The cosmetic formulation of this invention is used prophylactically to prevent the outbreak of herpetic lesions of the skin. The formulation can be applied nightly to susceptible areas of the skin. Generally, the cosmetic composition contains less of the peptide than corresponding pharmaceutical compositions for topical application. A preferred range of the amount of the peptide in the cosmetic composition is 0.01 to 0.2 percent by weight.

Although the formulations disclosed hereinabove are indicated to be effective and relatively safe medications for treating herpes viral infections, the possible concurrent administration of these formulations with other antiviral medications or agents to obtain beneficial results is not excluded. Such other antiviral medications or agents include the antiviral nucleosides, for example, acyclovir, and antiviral surface active agents or antiviral interferons such as those disclosed by S. S. Asculai and F. Rapp in U.S. Pat. No. 4,507,281, Mar. 26, 1985.

More specifically with respect to treating herpes viral infections by concurrent administration, it has been found that the antiherpes activity of an antiviral nucleoside analogs can be enhanced synergistically, without the concomitant enhancement of toxic effects, by combining the same with a peptide of formula 1. Accordingly, there is provided herewith a pharmaceutical composition for treating herpes infections in a mammal comprising a pharmaceutically or veterinarily acceptable carrier, and an effective amount of the combination of an antiviral nucleoside analog or a therapeutically acceptable salt thereof, and a ribonucleotide reductase inhibiting peptide of formula 1 or a therapeutically acceptable salt thereof.

Also provided herein is a method of treating herpes viral infections in a mammal. The method comprises administering to the mammal an antiherpes virally effective amount of a combination of a compound of formula 1 or a therapeutically acceptable salt thereof, and an antiviral nucleoside analog or a therapeutically acceptable salt thereof.

The antiviral nucleoside analog employed in the combination is one which is enzymatically convertible (in vivo) to a viral DNA polymerase inhibitor of, and/or an alternative substrate for, a herpes DNA polymerase. The antiviral nucleoside analog can be selected from known nucleoside analogs. Preferred nucleoside analogs of the invention include acyclovir and its analogs; for example, the compounds of formula 3 wherein $R^{14}$ is hydrogen, hydroxy or amino, or a therapeutically acceptable salt thereof. (Formula 2 wherein $R^{14}$ is hydroxy represents acyclovir.)

Other preferred antiviral nucleoside analogs for use according to the present invention include vidarabine, idoxuridine, trifluridine, ganciclovir, edoxudine, brovavir, fiacitabine, penciclovir, famciclovir and rociclovir.

The term "synergistic effect" when used in relation to the antiviral or antiherpes activity of the above defined combination of the nucleoside analog and peptide of formula 1 means an antiviral or antiherpes effect which is greater than the predictive additive effect of the two individual components of the combination.

When utilizing the combination of this invention for treating herpes infections, the combination is administered to warm blooded animals, e.g. humans, pigs or horses, in a vehicle comprising one or more pharmaceutically acceptable carriers, the proportion of which is determined by the solubility and chemical nature of the nucleoside analog and the peptide of formula 1, chosen route of administration, standard biological practice, and by the relative amounts of the two active ingredients to provide a synergistic antiviral effect. Preferably, the combination is administered topically. For example, the two active agents (i.e. the antiviral nucleoside analog and the peptide of formula 1, or their therapeutically acceptable salts) can be formulated in the form of solutions, emulsions, creams, or lotions in pharmaceutically acceptable vehicles. Such formulation can contain 0.01 to 1.0 percent by weight of the nucleoside analog, or a therapeutically acceptable salt thereof, and about 0.05 to 1 percent by weight of the peptide of formula 1, or a therapeutically acceptable salt thereof.

In any event, the two active agents are present in the pharmaceutical composition in amounts to provide a synergistic antiherpes effect.

The following examples illustrate further this invention. Temperatures are given in degrees Celsius. Solution percentages or ratios express a volume to volume relationship, unless stated otherwise. Nuclear magnetic resonance spectra were recorded on a Bruker 200 MHz or 400 MHz spectrometer (a 400 MHz spectrum being noted in the preamble); the chemical shifts (δ) are reported in parts per million. Abbreviations used in the examples include Boc: tert-butyloxycarbonyl; Bu: butyl; Bzl: benzyl; DMF: dimethylformamide; Et: ethyl; EtOH: ethanol; EtOAc: ethyl acetate; $Et_2O$: diethyl ether; Me: methyl; MeOH: methanol; Pr: propyl; TLC: thin layer chromatography; THF: tetrahydrofuran.

EXAMPLE 1

General Procedure for Coupling Reactions

{See also R. Knorr et al., Tetrahedron Letters, 30, 1927 (1989).}

The first reactant, i.e. a free amine (or its hydrochloride salt), is dissolved in $CH_2Cl_2$ or acetonitrile and the solution is cooled to 4°. Under a nitrogen atmosphere, four equivalents of N-methylmorpholine is added to the stirred solution. After 20 min., one equivalent of the second reactant, i.e. a free carboxylic acid, and 1.05 equivalent of the coupling agent are added. (Practical and efficient coupling reagents for this purpose are (benzotriazol-1-yloxy)tris(dimethylamino)phosphonium hexafluorophosphate or preferably 2-(1H-benzotriazol-1-yl)-N,N,N',N'-tetramethyluronium tetrafluoroborate.] The reaction is monitored by TLC. After completion of the reaction, the $CH_2Cl_2$ (or acetonitrile) is evaporated under reduced pressure. The residue is dissolved in EtOAc. The solution is washed successively with 1N aqueous citric acid, 10% aqueous $Na_2CO_3$ and brine. The organic phase is dried ($MgSO_4$), filtered and concentrated to dryness under reduced pressure. The residue is purified on silica gel ($SiO_2$) according to Still's flash chromatography technique {W. C. Still et al., J. Org. Chem., 43, 2923 (1978)}.

EXAMPLE 2

Preparation of the Intermediate H-Asp(cyPn)(Bzl)—NH—(S)—CH($CH_2CMe_3$)$CH_2OBzl$ (a) (S)-α-Azido-1-{(phenylmethoxy)carbonyl}-cyclopentaneacetic acid: This compound was prepared from 2-oxospiro[4.4]nonane-1,3-dione, described by M. N. Aboul-Enein et al., Pharm. Acta Helv., 55, 50 (1980), according to the asymmetric azidation method utilizing the Evan's auxiliary, see D. A. Evans et al., J. Amer. Chem. Soc., 112, 4011 (1990).

More explicitly, a 1.6M hexane solution of butyllithium (469 ml, 750 mmol) was added dropwise under an argon atmosphere to a solution of the chiral auxiliary, 4(S)-(1-methylethyl)-2-oxazolidinone, {96.8 g, 750 mmol, described by L. N. Pridgen and J. Prol., J. Org. Chem., 54, 3231 (1989)}in dry THF at −40°. The mixture was stirred at −40° for 30 min and then cooled to −78°. 2-Oxospiro[4.4]nonane-1,3-dione was added dropwise to the cooled mixture. The mixture then was stirred at 0° for 1 h. Thereafter, a 20% (w/v) aqueous solution of citric acid (600 mL) was added to the mixture. The organic phase was separated and the aqueous phase was extracted with EtOAc. The combined organic phases were washed with brine, dried ($MgSO_4$) and concentrated under reduced pressure to give 3-{2-(1-carboxycyclopentyl)-1-oxoethyl}-4(S)-(1-methylethyl)-2-oxazolidinone as a pink solid (300 g).

The latter solid (ca 750 mmol) was dissolved in acetonitrile (1 L). Benzyl bromide (128.3 g, 89.2 mL, 750 mmol) and 1,8-diazabicyclo[5.4.0]-undec-7-ene (114 g, 112 mL, 750 mmol) were added to the solution. The mixture was stirred under argon for 16 h. The volatiles were removed under reduced pressure. The residue was dissolved in $H_2O$/EtOAc. The organic phase was separated, washed with a 10% (w/v) aqueous solution of citric acid, brine, dried ($MgSO_4$) and concentrated to dryness under reduced pressure to give an oil. Crystallization of the oil from hexane/EtOAc gave the corresponding benzyl ester as a white solid (204 g, 73%).

A solution of the latter compound (70 g, 187 mmol) in dry THF (200 mL) was cooled to −78°. A 0.66 M THF solution of potassium 1,1,1,3,3,3-hexamethyldisilazane (286 mL, 189 mmol) containing 6% (w/v) cumene was added over a period of 15 min to the cooled solution. The mixture was stirred at −78° for 45 min. A solution of 2,4,6-triisopropylbenzenesulfonyl azide (67 g, 216 mmol) in dry THF (100 mL) was added in one portion to the cold mixture, followed two minutes later by the addition of glacial acetic acid (50 mL, 860 mmol). The mixture was warmed and stirred at 35°–45° for 1 h. The volatiles were removed under reduced pressure. The yellow residue was triturated with hexane/EtOH (4:1, 1.7 L). The resulting white solid was collected on a filter. The filtrate was mixed with $SiO_2$ (230–240 mesh). Volatiles were removed under reduced pressure and the residual solid was dried at 35° under reduced pressure to remove cumene. The residual solid then was placed on a column of $SiO_2$. Elution of residual solid and $SiO_2$ with hexane-EtOAc, 9:1 and concentration of the eluent gave 3-{{2(S)-azido-1-oxo-2-{1-{(phenylmethoxy)carbonyl}cyclopentyl}ethyl}-4(S)-(1-methylethyl)-2-oxazolidinone (66 g, 86%).

A solution of the latter compound (13.42 g, 32.4 mmol) in $THF/H_2O$ (3:1, 608 mL) was cooled to 0°. Hydrogen peroxide/$H_2O$ (3:7, 16.3 mL, 518 mmol of $H_2O_2$) was added to the cooled solution; followed by the addition of $LiOH \cdot H_2O$ (2.86 g, 68.2 mmol). The mixture was stirred at 0° for 45 min and then quenched with a 10% (w/v) aqueous solution of sodium sulfite (400 mL). After $NaHCO_3$ (1.93 g) had been added, the mixture was concentrated under reduced pressure. The chiral auxiliary was recovered by continuous extraction (aqueous $NaHCO_3$/chloroform) for 20 h. Thereafter, the aqueous phase was cooled to 0° rendered acidic by the addition of concentrated HCl and then extracted with EtOAc. The extract was washed with brine, dried ($MgSO_4$) and concentrated under reduced pressure to give the desired compound as a white solid (8.2 g, 84%). The $^1H$ NMR ($CDCl_3$) of the compound showed: $\delta$1.6–1.8 (m, 5H), 1.95–2.05 (m, 2H), 2.20–2.30 (m, 1H), 4.55 (s,1H), 5.12 (s,2H) and 7.4 (m,5H).

The compound is used in section (c) of this example.

(b) $NH_2$—(S)—$CH(CH_2CMe_3)CH_2OBzl$: H-γMeLeu-OH was reduced with $LiBH_4/Me_3SiCl$ according to the method of A. Giannis and K. Sandhoff, Angew. Chem. Int. Ed. Engl., 28, 218 (1989) to give the aminoalcohol $NH_2$—(S)—$CH(CH_2CMe_3)CH_2OH$. A mixture of the latter compound (812 mg, 6.2 mmol), triethylamine (659 mg, 6.51 mmol) and di-tert-butyl dicarbonate (1.42 g, 6.51 mmol) in dry THF (15 mL) was stirred under a nitrogen atmosphere at 4° for 15 min and then at room temperature for 4 h. The THF was evaporated under reduced pressure. The residue was dissolved in EtOAc. The solution was washed with 10% aqueous citric acid, 5% aqueous $NaHCO_3$ and brine. The organic phase was dried ($MgSO_4$) and concentrated to dryness under reduced pressure. The residue was purified by flash chromatography ($SiO_2$, eluent: hexane-EtOAc, 2:1) to give Boc-NH—(S)—$CH(CH_2CMe_3)$—$CH_2OH$ (1.23 g, 86%).

Tetrabutylammonium bisulfate (106 mg) and 50% aqueous NaOH (3 mL) were added successively to a solution of Boc-NH—(S)—$CH(CH_2CMe_3)CH_2OH$ (1.23 g, 5.35 mmol) in benzyl chloride (13 mL). The resulting mixture was stirred at 35°–40° for 90 min, diluted with EtOAc, and washed with $H_2O$ and brine. The organic phase was dried ($MgSO_4$) and concentrated to dryness under reduced pressure. The residue was dissolved in hexane. The solution was poured onto a column of $SiO_2$. The column was eluted with hexane to remove benzyl chloride, and then with hexane-EtOAc (2:1) to give Boc-NH—(S)—$CH(CH_2CMe_3)CH_2OBzl$. The $^1H$ NMR ($CDCl_3$) of the latter compound showed $\delta$ 0.95 (s,9H), 1.42 (s, 9H), 1.30–1.55 (m, 2H), 3.42 (d, J=4 Hz, 2H), 3.88 (broad, 1H), 4.54 (m, 3H), 7.23–7.4 (m, 5H). The latter compound (1.28 g, 3.99 mmol) was dissolved in 6N HCl/dioxane (10 mL). The solution was stirred under a nitrogen atmosphere at 4° for 45 min. Evaporation of the solvent gave the hydrogen chloride salt of the desired compound (1.05 g). The compound is used without further purification in the next section of this example.

(c) The title compound of this example: By following the coupling procedure of example 1 and using the hydrogen chloride salt of $NH_2$—(S)—$CH(CH_2CMe_3)CH_2OBzl$ of the preceding section as the first reactant and (S)-α-azido-1-{(phenylmethoxy)-carbonyl}cyclopentaneacetic acid of section (a) of this example as the second reactant, N-{(S)-1-benzyloxymethyl-3,3-dimethylbutyl}-(S)-α-azido-1-{(phenylmethoxy)carbonyl} cyclopentaneacetamide was obtained. Reduction of the latter compound with tin(II) chloride in MeOH according to the method of N. Maiti et al., Tetrahedron Letters, 27, 1423 (1986) gave the title compound of this example. The $^1H$ NMR ($CDCl_3$) of the compound showed $\delta$0.98 (s, 9H), 1.22–2.25 (m, 12H), 3.4 (d, J=4 Hz, 2H), 3.64 (s, 1H), 4.18 (broad m, 1H), 4.52 (s, 2H), 5.12 (s, 2H), 7.18 (d, J=7 Hz, 1H), 7.22–7.38 (broad m, 10H).

EXAMPLE 3

Preparation of the Intermediate Boc-Tbg-$CH_2$—(RS)—$CH(CH_2C(O)CMe_3)C(O)OH$ (a) Magnesium salt of monoallyl malonate: A solution of 2,2-dimethyl-1,3-dioxane-4,6-dione (100 g, 0.69 mol) and allyl alcohol (47 mL, 0.69 mol in benzene (800 mL) was heated at reflux for 24 h. The solvent was evaporated under reduced pressure. Distillation of the residue under reduced pressure gave monoallyl malonate (71 g, 71%, bp 123°–127°/2.7 mm Hg). The latter ester (71 g, 0.48 mol) was dissolved in dry THF (300 mL). Magnesium ethoxide (28.5 g, 0.245 mol) was added to the solution. The mixture was stirred under argon for 4 h at room temperature (20°–22°). The solvent was evaporated under reduced pressure and the residue was triturated with $Et_2O$ to give a tan solid. The solid was ground into fine particles and dried under reduced pressure to give the desired magnesium salt (56 g, 73%). The salt is used in the next section of this example.

(b) Boc-Tbg-$CH_2C(O)OCH_2$=$CH_2$: 1,1-Carbonyldiimidazole (12.6 g, 78 mmol) was added to a solution of Boc-Tbg-OH (15 g, 64 mmol) in dry acetonitrile (150 mL). The mixture was stirred under argon for 2 h at room temperature. The magnesium salt of monoallyl malonate (24 g, 78 mmol) and 4-(N,N-dimethylamino)pyridine (100 mg) were added to the mixture. The mixture was heated at reflux for 1 h and then stirred at room temperature for 18 h. Thereafter, the mixture was concentrated under reduced pressure. The residue was dissolved in EtOAc (300 mL). The solution was washed with 10% aqueous citric acid (2×100 mL) and brine (2×100 mL), dried ($MgSO_4$) and evaporated to dryness. The residue was purified by flash chromatography ($SiO_2$, eluent: hexane-EtOAc, 9:1) to give the desired allyl ester (19.4 g, 96%) as a brown oil which crystallized on standing. $^1H$ NMR ($CDCl_3$), note that this compound exists as a mixture of keto-enol tautomers in a 3:1 ratio in chloroform, $\delta$ 0.96 (s, 9H, enol form), 1.04 (s, 9H), 1.46 (s, 9H), 3.65 (s, 2H), 3.90 (d, J=8.5 Hz, 1H, enol form), 4.20 (d, J=7.5 Hz, 1H), 4.65 (m, 2H), 5.10 (broad d, J=7.5 Hz, 1H), 5.20–5.40 (m, 2H), 5.80–6.05 (m, 1H), 12 (s, 1H, enol form). The allyl ester is used in section (d) of this example.

(c) (E)-5,5-Dimethyl-4-oxo-2-hexenoic acid ethyl ester: This ethyl ester was prepared according to the method of S. Manfredini et al., Tetrahedron Letters, 29, 3997 (1988). The oily crude product was purified by flash chromatography (SiO$_2$, eluent: hexane) to give the desired ethyl ester as a yellow oil. $^1$H NMR (CDCl$_3$) δ 1.21 (s, 9H), 1.33 (t, J=7.5 Hz, 3H), 4.28 (q, J=7.5 Hz, 2H), 6.78 (d, J=15.5 Hz, 1H), 7.51 (d, J=15.5 Hz, 1H). The ethyl ester is used in the next section of this example.

(d) The title compound of this example: Boc-Tbg-CH$_2$C(O)OCH=CH$_2$ (0.67 g, 2.1 mmol), described in section (b) of this example, was dissolved in anhydrous THF (25 mL) under an argon atmosphere. Sodium hydride (60% oil dispersion, 0.095 g, 2.4 mmol) was added to the solution. The mixture was stirred at room temperature for 30 min. (E)-5,5-dimethyl-4-oxo-2-hexenoic acid ethyl ester (0.435 g, 2.36 mmol), described in section (c) of this example, was added to the mixture. The reaction mixture was stirred until the reaction was complete as judged by TLC (about 6 h). Thereafter, the mixture was quenched with 10% aqueous citric acid. THF was removed under reduced pressure and the resulting concentrate was extracted with EtOAc (3×25 mL). The extract was washed with H$_2$O, dried (MgSO$_4$) and concentrated under reduced pressure. The residue was purified by flash chromatography (SiO$_2$, eluent: hexane-EtOAc, 9:1) to give the corresponding Michael reaction adduct (1.06 g, 100%).

The Michael adduct was transformed to Boc-Tbg-CH$_2$—(RS)—CH(CH$_2$C(O)CMe$_3$)C(O)OH as follows: Tetrakistriphenylphosphine palladium(O) (0.20 g, 0.18 mmol) and triphenylphosphine (0.060 g, 0.23 mmol) were dissolved in CH$_2$Cl$_2$ (10 mL) under an argon atmosphere. Acetonitrile (20 mL) was added and the solution was cooled to 0°. Pyrrolidine (0.28 mL, 2.7 mmol) and then the Michael adduct (1.06 g, 2.1 mmol) were added to the solution. The mixture was allowed to come to room temperature over 1 h and then stirred for 20 h. Thereafter, the reaction mixture was heated at reflux for 1 h under argon to complete the reaction. The solvent was evaporated and the residue was purified by flash chromatography (SiO$_2$, eluent: hexane-EtOAc, 9:1) to give Boc-Tbg-CH$_2$—(RS)—CH(CH$_2$C(O)CMe$_3$)C(O)OEt (0.77 g, 83%). Thereafter, the latter compound (0.77 g, 1.7 mmol) was dissolved in ethyleneglycol dimethyl ether—H$_2$O (1:1, 10 mL). Lithium hydroxide monohydrate (0.31 g, 7.4 mmol) was added to the solution. The mixture was stirred at room temperature for 4 h, rendered acidic with 10% aqueous citric acid (20 mL) and extracted with EtOAc (3×25 mL). The extract was dried (MgSO$_4$) and concentrated under reduced pressure to give the title compound of this example as a tan solid (0.69 g, 80% yield overall from Boc-Tbg-CH$_2$C(O)O—CH$_2$CH=CH$_2$). The product was a 55:45 mixture of diastereoisomers (shown by NMR). $^1$H NMR (CDCl$_3$) δ 0.99 (s, 9H, minor isomer), 1.14 (s, 9H, major isomer), 1.43 (s, 9H), 2.68–3.12 (m, 4H), 3.30 (m, 1H), 4.09 (d, J=9 Hz, 1H), 5.11 (d, J=9 Hz, 1n).

EXAMPLE 4

Preparation of the Intermediate H-Tbq-CH$_2$CH(CH$_2$C(O)CMe$_3$)C(O)-Asp(cyPn)(Bzl)-NH—(S)—CH(CH$_2$CMe$_3$)CH$_2$OBzl By following the coupling procedure of example 1 and using the title compound of example 2(3.42 g, 7.13 mmol) as the first reactant and the title compound of example 3 (2.50 g, 6.48 mmol) as the second reactant, flash chromatography (SiO$_2$, eluent: hexane-EtOAc, 4:1) of the crude product gave the corresponding N-Boc derivative of the title compound (4.64 g, 84%; Rf=0.21, hexane-EtOAc, 7:3). A solution of the latter derivative (4.64 g, 5.44 mmol) in 6N HCl/dioxane (50 mL) was stirred at room temperature for 1 h and then concentrated under reduced pressure. The residue was dissolved in Et$_2$O. The latter solution was washed with saturated aqueous solution of NaHCO$_3$ and brine, dried (MgSO$_4$) and concentrated to give a yellow oil consisting of two diastereoisomers. The two isomers were separated by flash chromatography (SiO$_2$, eluent: hexane-EtOAc-MeOH, 5:4.5:0.5). The desired isomer (i.e. the more polar; Rf=0.18, EtOAc-hexane-MeOH, 7:3:0.5) was obtained as a colourless oil (2.52 g, 52%). The isomer, the title compound of this example, is used without further purification in the next example.

EXAMPLE 5

Preparation of Boc-(N-Me)Val-Tbq-CH$_2$(R)—CH(CH$_2$C(O)CMe$_3$)C(O)-Asp(cyPn) (Bzl)-NH—(S)—CH(CH$_2$CMe$_3$)CH$_2$OBzl By following the coupling procedure of example 1 and using the title compound of example 4(4.45 g, 5.95 mmol) as the first reactant and BOC-(N-Me)Val-OH (4.41 g, 17.9 mmol) as the second reactant, flash chromatography (SiO$_2$, eluent: hexane-EtOAc, 7:3) of the crude product gave the title compound of this example (4.02 g, 72% yield). $^1$H NMR (CDCl$_3$) δ 0.87 (d, J=7 Hz, 6H), 0.90 (s, 18H), 1.10 (s, 9H), 1.48 (s, 9H), 1.5–2.0 (m, 10H), 2.30 (m, 1H), 2.5–3.1 (m, 5H), 2.80 (s, 3H), 3.30 (m, 2H), 4.0 (d, J=12.5 Hz, 1H), 4.20 (m, 1H), 4.32 (d, J=8.5 Hz, 1H), 4.49 (d, J=4.5 Hz, 2H), 4.64 (d, J=11 Hz, 1H), 5.18 (d, J=5 Hz, 2H), 6.78 (broad d, J=8.5 Hz, 1H), 7.11 (broad d, J=8.5 Hz, 1H), 7.18 (broad d, J=11 Hz, 1H), 7.2–7.45 (m, 10H).

EXAMPLE 6

Preparation of PhCH$_2$CH$_2$C(O)—(N-Me)Val-Tbq-CH$_2$—(R)—CH(CH$_2$C(O)CMe$_3$)C(O)-Asp(cyPn)-γMeLeucinol A solution of the title compound of example 5 (4.02 g, 4.25 mmol) in 6N HCl/dioxane (30 mL) was stirred at room temperature for 1 h and then concentrated under reduced pressure to give the free N-terminal amino derivative of the title compound of example 5 in the form of its hydrochoride salt. Thereafter, by following the coupling procedure of example 1 and using the latter amino derivative as the first reactant and benzenepropionic acid (2.00 g, 13.3 mmol) as the second reactant, the purification of the crude product by flash chromatography (SiO$_2$, eluent: hexane-EtOAc, 3:2) gave PhCH$_2$CH$_2$C(O)—N-Me-Val-Tbg-CH$_2$—(R)—CH(CH$_2$C(O)CMe$_3$)C(O)-Asp-(cyPn) (OBzl)-NH—(S)—CH(CH$_2$CMe$_3$)CH$_2$OBzl as a white foam (4.00 g, 94%; Rf=0.35, hexane-EtOAc, 1:1). $^1$H NMR (CDCl$_3$, 400 MHz) δ 0.79 (d, J=7 Hz, 3H), 0.91 (s, 9H), 0.93 (s, 9H), 1.08 (s, 9H), 1.5–1.9 (m, 10H), 2.27 (m, 1H), 2.5–2.85 (m, 7H), 2.90 (s, 3H), 2.97 (m, 4H), 3.27 (dd, J=11, 7 Hz, 1H), 3.55 (dd, J=11, 4.5 Hz, 1H), 3.48 (q, J=7.5 Hz, 2H), 4.22 (m, 1H), 4.27 (d, J=8 Hz, 1H), 4.48 (1, J=8.5 Hz, 2H), 4.53 (d, J=11 Hz, 1H), 4.63 (d, J=0.5 Hz, 1H), 5.16 (q, J=13 Hz, 2H), 6.72 (d, J=8 Hz, 1H), 7.02 (d, J=8.5 Hz, 1H), 7.17 (d, J=9.5 Hz, 1H), 7.18–7.4 (m, 10H).

The latter compound (4.00 g, 4.03 mmol) was subjected to hydrogenolysis {20% Pd(OH)$_2$/C (200 mg), 1 atmosphere of H$_2$, EtOH, 5 h}. After completion of the reaction, the catalyst was removed from the reaction mixture by filtration through a 45 μm membrane. The filtrate was concentrated under reduced pressure to give a clear oil. The oil was dissolved in Et$_2$O (100 mL). The solution was evaporated to dryness under reduced pressure. The dissolving and evaporating process was repeated whereby a white solid was obtained. The solid was triturated with hexane, filtered and dried under reduced pressure to give the title compound(3.12 g, 95%) $^1$H NMR (d$_6$-DMSO), 400 MHz; note: the compound exists in DMSO as a 50:50 mixture of two rotamers δ 0.71–0.92 (m, 24H), 1.05 (s, 4.5H), 1.06 (s, 4.5H), 1.20–1.78 (m, 10H), 1.93–2.16 (m, 2H), 2.48–2.83 (m, 6H), 2.84 (s, 1.5H), 2.92 (s, 1.5H), 2.96–3.06 (m, 1H), 3.10–3.23 (m, 2H), 3.72–3.81 (m, 1H), 4.09–4.14 (m, 1H), 4.22 (d, 8 Hz, 0.5H), 4.54–4.62 (broad m, 1H), 4.73–4.81 (m, 1.5H), 7.12–7.29 (m, 6H), 7.94 (d, J=10 Hz, 1H), 8.04 (d, J=8 Hz, 0.5H), 8.32 (d, J=8.5 Hz, 0.5H).

By following the procedure of example 6 but replacing benzenepropionic acid with 2-(phenyl-methyl)-3-phenyl-propionic acid (dibenzylacetic acid), (PhCH$_2$)$_2$CHC(O)-(N-Me)Val-Tbg-CH$_2$—(R)—CH(CH$_2$C(O)-CMe$_3$)C(O)-Asp-(cyPn)-γMeLeucinol is obtained.

EXAMPLE 7

Preparation of Et$_2$CHNHC(O)-Tbq-CH$_2$—(R)—CH(CH$_2$C(O)CMe$_3$)CO-Asp(cyPn)-γMeLeucinol 1-Ethylpropyl isocyanate (28 mg, 0,248 mmol) was added to a solution of the title compound of example 4 (23 mg, 0.030 mmol) and triethylamine (6 mg, 0,057 mmol) in anhydrous CH$_2$Cl$_2$. The reaction mixture was stirred under an argon atmosphere at 0° for 1 h and then at room temperature for 18 h. TLC (EtOAc-hexane, 1:1) indicated the completion of the reaction. The solvent was evaporated under reduced pressure. The residue was purified by flash chromatography (SiO$_2$, eluent: hexane-EtOAc, 6:4) to give the corresponding dibenzyl derivative of the title compound of this example (16 mg). $^1$H NMR (400 MHz, CDCl$_3$) δ 0.9 (t, J=7 Hz, 3H), 0.92 (t, J=7 Hz, 3H), 0.94 (s, 9H), 0.95 (s, 9H), 1.10 (s, 9H), 1.25–1.90 (m, 14H), 2.52 (m, 1H), 2.68 (m, 1H), 2.81 (m, 1H), 2.94–3.07 (m, 2H), 3.27 (dd, J=7.2, 9 Hz, 1H), 3.36 (dd, J=5.5, 9 Hz, 1H), 3.46 (m, 1H), 4.07 (d, J=9 Hz, 1H), 4.23 (m, 1H), 4.28 (d, J=9 Hz, 1H), 4.48 (dd, J=10 Hz, 2H), 4.66 (d, J=10 Hz, 1H), 4.74 (d, J=9 Hz, 1H), 5.17 (dd, J=14 Hz, 2H), 7.10 (d, J=8.5 Hz, 1H), 7.2–7.45 (m, 11H).

The latter dibenzyl derivative was subjected to hydrogenolysis (10% palladium on carbon, 1 atmosphere, EtOH) to give the title compound. Mass spectrum: 703 (M+Na)$^+$.

EXAMPLE 8

Preparation of Other Representative Intermediates for the Elaboration of the C-Terminus of Peptides of Formula 1.

(a) NH$_2$—(R)—CH(Et)CMe$_3$: To a cooled solution (0°) of 4,4-dimethyl-3-pentanone (106 g, 0.92 mmol) and (R)-α-methylbenzylamine (111 g, 0.92 mmol) in benzene (1 L), a solution of TiCl$_4$ (50.5 mL, 0.46 mmol) in benzene (200 mL) was added at a rate that kept the temperature of the mixture below 10°. Thereafter, the mixture was stirred mechanically for 3 h at 40°, cooled to room temperature and filtered through diatomaceous earth. The diatomaceous earth was washed with Et$_2$O. The combined filtrate and wash was concentrated. The residue was dissolved in dry MeOH (2 L). The solution was cooled to 0° and NaBH$_4$ (20 g, 0.53 mmol) was added portionwise while maintaining the temperature of the mixture below 5°. The methanol was evaporated. The residue was dissolved in Et$_2$O. The solution was washed with brine, dried (MgSO$_4$) and evaporated to dryness to give a reddish oil (a 18:1 mixture of diastereoisomers as indicated by NMR). The oil was purified by flash chromatography (SiO$_2$, eluent: EtOAc/hexane, 7:93) to afford N-(1(R)-phenylethyl)-1(R)-ethyl-2,2-dimethylpropyl-amine as a liquid (110 g, 54%). This material was dissolved in hexane (1.5 L). 6N HCl in dioxane (90 mL) was added to the solution over a period of 15 min. The resulting white solid was collected on a filter and then washed with hexane to provide N-(1(R)-phenyl-ethyl)-1(R)-ethyl-2,2-dimethylpropylamine hydrochloride (125 g, 97%). $^1$H NMR(CDCl$_3$) δ 0.55 (t, J=7.5 Hz, 3H), 1.14 (s, 9H), 1.54–1.95 (m, 2H), 2.23 (d, J=6.5 Hz, 3H), 2.36–2.44 (m, 1H), 4.31–4.49 (m, 1H), 7.30–7.48 (m, 3H), 7.74–7.79 (m, 2H).

A solution of the latter compound (41.5 g) in MeOH (120 mL) was mixed with 10% (w/w) Pd/C and the mixture was shaken under 50 psi of hydrogen on a Parr hydrogenator at room temperature for 48 h. The mixture was filtered and the filtrate was concentrated to give the desired NH$_2$—(R)—CH(Et)C-Me$_3$ in the form of its hydrochloric acid addition salt, as a white solid (25 g, 100%). $^1$H NMR(CDCl$_3$) δ 1.10 (s, 9H), 1.22 (t, J=7 Hz, 2H), 1.58–1.90 (m, 2H), 2.70–2.85 (m, 1H), 8.10–8.40 (broad s, 3H).

In the same manner but replacing 4,4-dimethyl-3-pentanone with 3,3-dimethyl-2-butanone in the preceding procedure, NH$_2$—(R)—CH(Me)CMe$_3$.HCl is obtained.

(b) NH$_2$N(Me)CMe$_3$: NaOH (3.3 g, 82 mmol) was added to a solution of tert-butylhydrazine hydrochloride (5.1 g, 41 mmol). After 15 min, a solution of di-tert-butyl dicarbonate (9.0 g, 42 mmol) in THF (15 mL) was added to the mixture. The mixture was stirred at room temperature for 15 h and then extracted with Et$_2$O (3×20 mL). The combined extracts were washed with a saturated aqueous solution of Na$_2$CO$_3$, dried (MgSO$_4$) and concentrated to afford a white solid (7.6 g). The latter material (1.3 g, 6.9 mmol) was dissolved in dry DMF. A 60% (w/w) dispersion of NaH in mineral oil (0.28 g, i.e. 6.9 mmol of NaH) and then DMF (1.5 mL) were added to the solution. After the mixture had been stirred for 20 min, neat methyliodide (0.97 g, 6.9 mmol) was added. The reaction mixture was stirred at room temperature for 15 h and then partitioned between H$_2$O and Et$_2$O. The organic phase was separated and washed with 0.5 N aqueous HCl (2×). The combined aqueous phases were rendered basic with NaHCO$_3$ and extracted with EtOAc (3×). The EtOAc extract was dried (MgSO$_4$) and concentrated to dryness to afford Boc-NHN(Me)CMe$_3$ as a white solid (0.9 g, 64%); $^1$H NMR(CDCl$_3$) δ 1.07 (s, 9H), 1.44 (s, 9H), 2.43 (s, 3H), 5.29 (s, 1H). The latter solid (0.9 g) was dissolved in 6N HCl/dioxane (5 mL). The solution was allowed to stand at room temperature for 30 min and then concentrated to dryness. Trituration of the residue with hexane afforded NH$_2$N(CH$_3$)CMe$_3$.HCl as a white solid (0.5 g). In the same manner but replacing methyl iodide with ethyl iodide in the preceding procedure, NH$_2$N (Et)-CMe$_3$.HCl, mp 129°–134°, is obtained.

EXAMPLE 9

Preparation of Other Representative Intermediates for Elaborating the N-Terminus of Peptides of Formula 1 According to the Procedure of Example 7.

(a) 1-Propylbutyl isocyanate: This intermediate was prepared from commercially available 4-aminoheptane by the procedure of V. S. Goldesmidt and M. Wick, Liebigs Ann. Chem., 575, 217 (1952).

(b) 1-Ethyl-1-(2-propenyl)-3-butenyl isocyanate: A solution of propionitrile (14.5 g, 264 mmol) in dry Et$_2$O (40 mL) was added dropwise to 1.0M allyl magnesium bromide/Et$_2$O (880 mL). The reaction mixture was mechanically stirred at reflux for 2 h, after which time it was cooled to 0°. A saturated aqueous solution of NH$_4$Cl (320 mL) was added cautiously to the cooled reaction mixture. The organic phase was separated, dried (MgSO$_4$), cooled to 0° and then mixed at the same temperature with 1M HCl/Et$_2$O (200 mL). The resulting solid was collected and dried under reduced pressure (ca 27 g). The latter material dissolved in $CH_2Cl_2$ (200 mL). The solution was washed with a 10% (w/v) aqueous solution of $Na_2CO_3$ (2×) and then brine, dried ($MgSO_4$) and concentrated to dryness to afford a yellow oil. The oil was distilled (82°–85°/20 Torr) to give 1-ethyl-1-(2-propenyl)-3-butenylamine as a colorless liquid (11.6 g, 34%); $^1$H NMR($CDCl_3$), 400 MHz $\delta$ 0.89 (t, J=7 Hz, 3H), 1.39 (q, J=7 Hz, 2H), 2.11 (d, J=7 Hz, 2H), 5.06–5.14 (m, 4H), 5.80–5.89 (m, 2H ).

The latter compound was converted to 1-ethyl-1-(2-propenyl)-3-butenyl isocyanate by the procedure of V. S. Goldesmidt and M. Wick, supra.

The first step of the process of preceding section b, i.e. the preparation of 1-ethyl-1-(2-propenyl)-3-butenylamine, is based on a general method described by G. Alvernhe and A. Laurent, Tetrahedron Lett., 1057 (1973). The overall process, with the appropriate choice of reactants, can be used to prepare other requisite isocyanate intermediates for the eventual preparation of peptides of formula 1 having unsaturation at the N-terminus, i.e. peptides of formula 1 wherein A-B is an unsaturated alkylaminocarbonyl of the formula $R^5$—NH—C(O) wherein $R^5$ is a branched unsaturated hydrocarbon radical such as 1-methyl-1-(2-propenyl)-3-butenyl. Note, however, that when the requisite isocyanate intermediates are applied according to the procedure of example 7, then the ultimate product will be the corresponding peptide of formula 1 in which the N-terminus is saturated. Moreover, the latter procedure represents a practical process for preparing such corresponding peptides; for example, $MePr_2CNHC(O)$— or $EtPr_2-CNHC(O)$-Tbg-$CH_2$—(R)—$CH(CH_2C(O)CMe_3)C(O)$-Asp(cyPn)-NHCH$_2CMe_3$, see the 8th and the 5th compounds listed in Table IV of example 13, respectively.

On the other hand, when it is desired to retain the unsaturation at the N-terminus, the N-terminal unsaturated peptides of formula 1 can be prepared in the same manner as for the corresponding saturated peptides provided that one employs carboxy protective groups which can be selectively removed in the presence of the unsaturation. A practical carboxy protective group for this purpose is the allyl group. Accordingly, the desired N-terminus unsaturated peptides can be prepared by following the procedure of examples 2 to 4 and 7 but replacing (S)-α-azido-1-{(phenylmethoxy)carbonyl}cyclopentanoic acid of example 2 with (S)-α-azido-1-(2-propenyloxycarbonyl)-cyclopentanoic acid. The latter compound has been prepared in exactly the same manner as described for the phenylmethoxy derivative in example 2(a) except that benzyl bromide was replaced with allyl bromide. The final deprotection step (i.e. the removal of the carboxy protective group, or groups in the instance wherein E of the target peptide is $NHCH(R^{12})$—Z wherein $R^{12}$ is as defined herein and Z is C(O)OH, can be accomplished accordingly to the procedure of R. Déziel, Tetrahedron Lett., 28, 4371 (1987), preferably with pyrrolidine in the presence of tetrakis(triphenylphosphine)palladium(0). An example of an N-terminal unsaturated peptide of formula 1 thus prepared is $Me(CH_2=CH—CH_2)_2CNHC(O)$-Tbg-$CH_2$—(R)—$CH(CH_2C(O)CMe_3)C(O)$-Asp(cyPn)-$NHCH_2CMe_3$, see the 7th compound listed in Table IV of example 13.

Note also that when E of the target N-terminal unsaturated peptide represents $NHCH(R^{10})$—Z wherein $R^{10}$ is as defined herein and Z is $CH_2OH$, the intermediate used to incorporate the hydroxy bearing C-terminus unit into the desired peptide requires protection for the nascent C-terminal hydroxyl. The hydroxy protective group in this instance should also be one which can be selectively removed in the presence of the unsaturation. A convenient protective group in this instance is the allyoxy-carbonyl group, see E. J. Corey and J. W. Suggs, J. Org. Chem., 38 3223 (1973).

Thus, by using the appropriate intermediates, the serial coupling and the deprotection procedures of examples 1 to 7 can be used to prepare other compounds of formula 1, such as those exemplified in the table of the following example. In some cases, precipitation of the final product does not afford pure material. In those instances, the product can be purified by semi preparative HPLC on a C-18 reversed-phase column using a gradient of acetonitrile and water, each containing 0.06% TFA. To this end, the crude product was dissolved in 0.1 M aqueous $NH_4OH$ and the pH of the solution was brought back to about 7 using 0.1 M aqueous AcOH, prior to purification. When applicable, diastereoisomeric mixtures were separated in this fashion.

Some examples of other compound of formula 1 that can be prepared thus are $(PhCH_2)_2CHC(O)$-(N-Me)Val-Tbg-$CH_2$—(R)—$CH(CH_2C(O)CMe_3)C(O)$-Asp(cyPn)-NHCH$_2CMe_3$ and $(PhCH_2)_2CHC(O)$—(N-Me)Val-Tbg-$CH_2$—(R)—$CH(CH_2C(O)CMe_3)C(O)$-Asp(cyPn)-NH—(R)—$CH(Me)CMe_3$.

EXAMPLE 10

Inhibition of Herpes Simplex Virus (HSV-1) Ribonucleotide Reductase a) Preparation of Enzyme HSV-1 ribonucleotide reductase (partially purified) was obtained from quiescent BHK-21/C13 cells infected with strain F HSV-1 virus at 10 plaque forming units/cell as described by E. A. Cohen et al., J. Gen. Virol., 66, 733 (1985).

b) Assay and Results for Exemplified Peptides

By following the procedure described by P. Gaudreau et al., J. Biol, Chem., 262, 12413 (1987), the assay results listed in the following Table I were obtained. The assay result for each exemplified compound of formula 1 is expressed as the concentration of the compound producing 50% of the maximal inhibition ($IC_{50}$) of enzyme activity. The number of units of the enzyme preparation used in each assay was constant, based on the specific activity of the enzyme preparation. The results are relative to the activity obtained in control experiments without the test compound and represent the mean of four assays that varied less than 10% with each other.

TABLE I

| Compound of Formula 1 | FAB/MS (m/z) (M + Na)$^+$ | $IC_{50}$ μM |
|---|---|---|
| Title Compound of Example 6 | 813* | 0.27 |
| $PhCH_2CH_2C(O)$—(N—Me)Val—Tbg—$CH_2$(R)-$CH(CH_2C(O)CMe_3)C(O)$—Asp(cyPn)— | 849 | 0.19 |

TABLE I-continued

| Compound of Formula 1 | FAB/MS (m/z) (M + Na)+ | IC$_{50}$ μM |
|---|---|---|
| γMeLeu—OH PHCH$_2$CH$_2$C(O)—(N—Me)Val—Tbg—CH$_2$—(R)-CH(CH$_2$C(O)CMe$_3$)C(O)—Asp(cyPn)—γMeLeu—NH$_2$ | 848 | 0.26 |
| PhCH$_2$CH$_2$C(O)—(N—Me)Val—Tbg—CH$_2$—(R)-CH(CH$_2$C(O)CMe$_3$)C(O)—Asp(cyPn)—NHCH$_2$CMe$_3$ | 791 | 0.33 |
| PhCH$_2$CH$_2$C(O)—(N—Me)Val—Tbg—CH$_2$—(R)-CH{CH$_2$C(O)—(cyclopentyl)}C(O)—Asp—(cyPn)—NHCH$_2$CMe$_3$ | 803 | 0.32 |
| PhCH$_2$CH$_2$C(O)—(N—Me)Val—Tbg—CH$_2$—(R)-CH(CH$_2$C(O)CMe$_3$)C(O)—Asp{(R)-Me}—NHCH$_2$CMe$_3$ | 751.5 | 0.33 |
| Et$_2$CHNHC(O)—Tbg—CH$_2$—(R)-CH(CH$_2$C(O)CMe$_3$)C(O)—Asp(cyPn)—NHCH$_2$CMe$_3$ | 659 | 0.23 |
| Et$_2$CHNHC(O)—Tbg—CH$_2$—(S)-CH{CH$_2$C(O)(pyrrolidino)}C(O)—Asp(cyPn)—γMeLeucinol | 716 | 0.17 |
| Et$_2$CHNHC(O)—Tbg—CH$_2$—(R)-CH(CH$_2$C(O)CMe$_3$)C(O)—Asp(cyPn)—γMeLeu—OH | 717 | 0.12 |
| Et$_2$CHNHC(O)—Tbg—CH$_2$—(R)-CH(CH$_2$C(O)CMe$_3$)C(O)—Asp(cyPn)—γMeLeu—NH$_2$ | 716 | 0.22 |
| Title Compound of Example 7 | 703 | 0.15 |
| Et$_2$CHNHC(O)—Tbg—CH$_2$—(R)-CH{CH$_2$C(O)(cyclopentyl)}C(O)—Asp(cyPn)—NHCH$_2$CMe$_3$ | 671 | 0.22 |
| Et$_2$CHNHC(O)—Tbg—CH$_2$—(R)-CH(CH$_2$C(O)CMe$_3$)C(O)—Asp{(R)-Me}—NHCH$_2$CMe$_3$ | 597* | 0.20 |
| Pr$_2$CHNHC(O)—Tbg—CH$_2$—(R)-CH(CH$_2$C(O)CMe$_3$)C(O)—Asp(cyPn)—γMeLeu—OH | 745 | 0.15 |
| Pr$_2$CHNHC(O)—Tbg—CH$_2$—(R)-CH(CH$_2$C(O)CMe$_3$)C(O)—Asp(cyPn)—γMeLeucinol | 731 | 0.20 |
| Pr$_2$CHNHC(O)—Tbg—CH$_2$—(R)-CH(CH$_2$C(O)CMe$_3$)C(O)—Asp(cyPn)—NHCH$_2$CMe$_3$ | 665* | 0.08 |

*(M + H)+

EXAMPLE 11

Inhibition of Herpes Simplex Virus (HSV-2). Replication in Cell Culture

Assay:

BHK-21/C13 cells (ATCC CCL 10) are incubated for two days in 150 cm$^2$ T-flasks (1.5×10$^6$ cells/flask) with alpha-MEM medium (Gibco Canada Inc., Burlington, Ontario, Canada) supplemented with 8% (v/v) fetal bovine serum (FBS, Gibco Canada Inc.). The cells are trypsinized and then transferred to fresh media in a 24 well plate to give 2.5×10$^5$ cells in 750 μL of media per well. The cells are incubated at 37° for a period of 6 h to allow them to adhere to the plate. Thereafter, the cells are washed once with 500 μL of alpha-MEM supplemented with 0.5% (v/v) FBS and then incubated with 750 μL of the see media (low serum) for 3 days. After this period of serum starvation, the low serum medium is removed and the cells are incubated in 500 μL of BBMT for 2 to 3 hours. {BBMT medium is described by P. Brazeau et al., Proc. Natl. Acad. Sci. USA, 79, 7909 (1982).} Thereafter, the cells are infected with HSV-2 (multiplicity of infection=0.02 PFU/cell) in 100 μL of BBMT medium. (Note: The HSV-2 used was strain HG-52, see Y. Langelier and G. Buttin, J. Gen. Virol., 57, 21 (1981); the virus was stored at −80°) Following 1 h of virus adsorption at 37°, the media is removed and the cells are washed with BBMT (3×250 μL). The cells in each well are incubated with or without (control) appropriate concentrations of the test agent dissolved in 200 μL of BBMT medium. After 29 h of incubation at 37°, the infected cells are harvested by first freezing the plate at −80°, followed by thawing. The cells in each well are scraped off the surface of the well with the help of the melting ice fragments. After complete thawing, the cell suspensions are collected and each well is rinsed with 150 μL of BBMT medium. The viral sample (suspension plus washing) is sonicated gently for 4 min at 4°. Cell debris are removed by centrifugation (1000 times gravity for 10 minutes at 4°). The supernatant is collected and stored at −80° until determination of viral titer.

Viral titration was performed by a modification of the colorimetric assay method of M. Langlois et al., Journal of Biological Standardization, 14, 201 (1986).

More specifically, in a similar manner as described above, BHK-21/C13 cells are trypsinized and transferred to fresh media in a 96 well microtiter plate to give 20,000 cells in 100 μL of media per well. The cells in the prepared plate are incubated at 37° for 2 h. During that time, the viral sample is thawed and sonicated gently for 15 seconds, and log dilutions of the sample are prepared (1/5 sequential: 50 μL of the sample plus 200 μL of BBMT medium, sequential dilutions being done with a multichannel pipette.

On completion of the above 2 hour incubation of the BHK-21/C13 cells, the media is replaced with alpha-MEM medium supplemented with 3% (v/v) FBS. The cells are now ready to be infected with the various sample dilutions of virus. Aliquots (50 μL) of the various dilutions are transferred into the appropriate wells of the plate. The resulting infected cells are incubated for 2 days at 37°. Then 50 μL of a 0.15% (v/v) solution of neutral red dye in Hank's Balanced Salt Solution (pH 7.3, Gibco Canada Inc.) is added to each well. The prepared plate is incubated for 45 min at 37°. Medium from each well is then aspirated and the cells are washed once with 200 μL of Hank's Balanced Salt Solution. After the wash, the dye is released from the cells by the addition of 100 μL of a 1:1 mixture of 0.1M Sorensen's citrate buffer (pH 4.2) and ethanol. {Sorensen's citrate buffer is prepared as follows: Firstly, a 0.1M disodium citrate solution is prepared by dissolving citric acid monohydrate (21 g) in 1N aqueous NaOH (200 mL) and adding sufficient filtered $H_2O$ to make 1 L. Secondly, the 0.1M disodium citrate solution (61.2 mL) is mixed with 0.1N aqueous HCl (38.8 mL) and the pH of the resulting solution is adjusted to 4.2 if necessary.} The mixture in the wells is subjected to a gentle vortex action to ensure proper mixing. The plate wells are scanned by a spectrophotometer plate reader at 540 μm to assess the number of viable cells. In this manner, the percentage of virus growth inhibition can be determined for the various concentrations of the test agent, and the concentration of the test agent effecting a 50% inhibition of virus replication, i.e. the $EC_{50}$ can be calculated.

Results:

The following Table II provides examples of the results obtained when peptides of formula 1 were evaluated according to the cell culture assay of this example.

TABLE II

| Compound of Formula 1 | $EC_{50}$ μM |
|---|---|
| Title Compound of Example 6 | 15 |
| PhCH₂CH₂C(O)—(N—Me)Val—Tbg—CH₂—(R)-CH(CH₂C(O)CMe₃)C(O)—Asp(cyPn)—γMeLeu—OH | 65 |
| PhCH₂CH₂C(O)—(N—Me)Val—Tbg—CH₂—(R)-CH(CH₂C(O)CMe₃)C(O)—Asp(cyPn)—γMeLeu—NH₂ | 60 |
| Et₂CHNHC(O)—Tbg—CH₂—(R)-CH(CH₂C(O)CMe₃)C(O)—Asp(cyPn)—NHCH₂CMe₃ | 56 |
| Et₂CHNHC(O)—Tbg—CH₂—(S)-CH{CH₂C(O)(pyrrolidino)}C(O)—Asp(cyPn)—γMeLeucinol | 200 |
| Et₂CHNHC(O)—Tbg—CH₂—(R)-CH{CH₂C(O)(cyclopentyl)}C(O)—Asp(cyPn)—NHCH₂CMe₃ | 50 |
| Pr₂CHNHC(O)—Tbg—CH₂—(R)-CH(CH₂C(O)CMe₃)C(O)—Asp(cyPn)—γMeLeucinol | 30 |
| Pr₂CHNHC(O)—Tbg—CH₂—(R)-CH(CH₂C(O)CMe₃)C(O)—Asp(cyPn)—NHCH₂CMe₃ | 24 |
| (1—propylcyclopentyl)aminocarbonyl-Tbg—CH₂—(R)-CH(CH₂C(O)CMe₃)C(O)—Asp(cyPn)—NHCH₂CMe₃ | 40 |
| Pr₂CHNHC(O)—Tbg—CH₂—(R)-CH{CH₂C(O)(cyclopentyl)}C(O)—Asp(cyPn)—NHCH₂CMe₃ | 30 |

EXAMPLE 12

Comparison of Acyclovir the Title Peptide of Formula 1 of Example 6 and the Combination of the Two Agents in Inhibiting HSV-2 Replication in Cell Culture The following Table III is illustrative of the results obtained when acyclovir and the title peptide of example 6 and combinations of the two were evaluated according to the assay procedure of example 11.

TABLE III

| COMPOUND | RANGE OF SAMPLE CONCENTRAT(ONS EVALUATED | $EC_{50}$ μM |
|---|---|---|
| acyclovir* | 0.032 to 20 μM | 3.5 |
| peptide** | 1.23 to 100 μM | 19 |
| acyclovir + 2 μM of peptide | 0.32 to 20 μM | 1.4 |
| acyclovir + 4 μM of peptide | 0.32 to 20 μM | 0.9 |
| acyclovir + 6 μM of peptide | 0.32 to 20 μM | 0.9 |
| acyclovir + 8 μM of peptide | 0.32 to 20 μM | 0.8 |
| acyclovir + 10 μM of peptide | 0.32 to 20 μM | 0.42 |

*acyclovir was obtained from Biuroughs Wellcome Inc., Kirkland, Quebec, Canada
**The title peptide of formula 1 of example 6.

The results demonstrate a synergistic action between acyclovir and the peptide of formula 1 in that the addition to the peptide to acyclovir affords combinations with $EC_{50}$'s significantly lower than the $EC_{50}$ of acyclovir alone.

Figure 1:
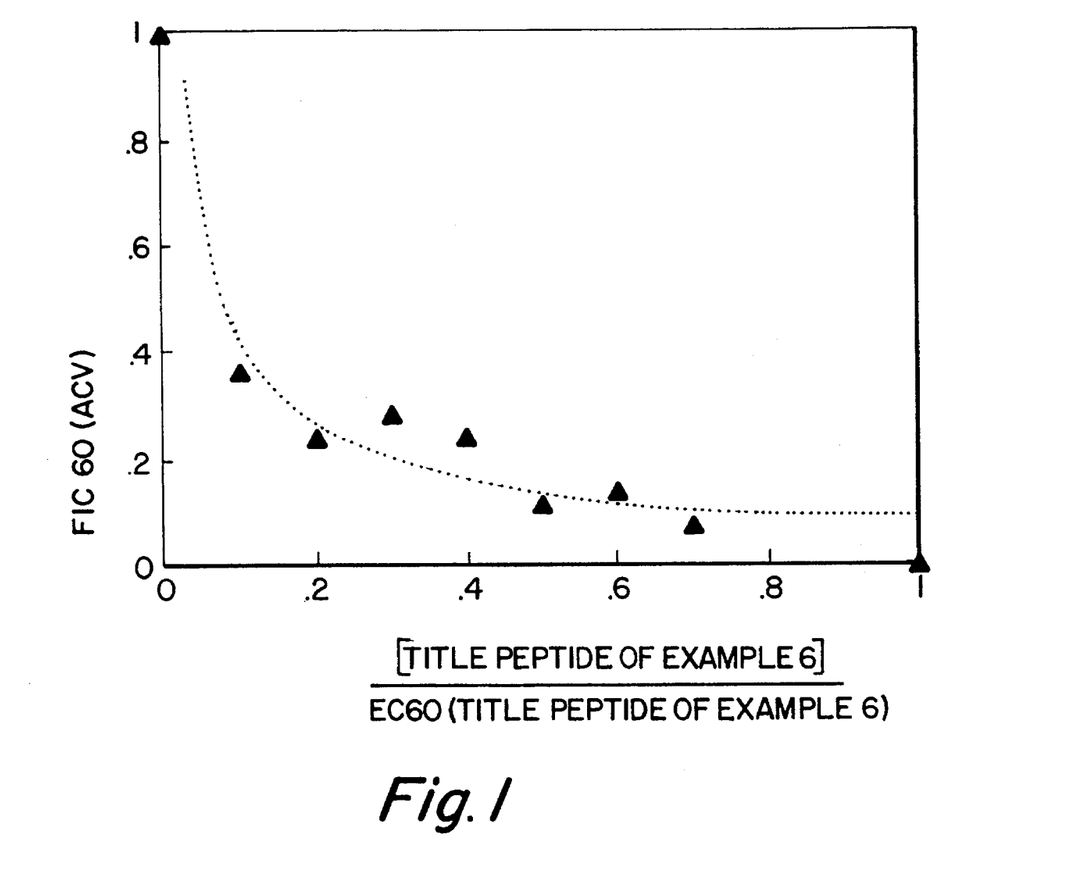
FIG. 1 is a graphic illustration of synergistic effect of various combinations of the peptide $PhCH_2CH_2C(O)$-(N-Me)Val-Tbg-$CH_2$—(R)—$CH(CH_2C(O)CMe_3)C(O)$-Asp-(cyPn)-γMeLeucinol and acyclovir for inhibiting HSV-2 replication in cell culture using the isobole method.

The synergism of the combination of acyclovir and the peptide of formula 1 can further be demonstrated by applying the isobole method to the above results, see J. Sühnel, Antiviral Research, 13, 23 (1990) and references therein. The positive result obtained in the application of this method is illustrated graphically in the accompanying FIG. 1.

EXAMPLE 13

Still other examples of peptides of formula 1 of this application are included in the following Tables IV and V together with characterizing mass spectra data and assay results in the assay of example 10, i.e. the $IC_{50}$; and the cell culture assay of example 11, i.e the $EC_{50}$.

TABLE IV

Compounds of Formula 1 having the formula A—B—Tbg—CH₂—(R)-CH—(CH₂C(O)cMe3C(O)—Asp(cyPn)—E wherein A—B and E are designated as follows:

| A—B | E | FAB/MS (m/z) (M + H)⁺ | $IC_{50}$ μM | $EC_{50}$ μM |
|---|---|---|---|---|
| Pr₂CHNHC(O) | NH—(R)-CH(Me)CMe₃ | 679 | 0.28 | 14 |
| Pr₂CHNHC(O) | NHCH₂CMe₂Et | 679 | 0.24 | 16 |
| Pr₂CHNHC(O) | NHCH₂—(R,S)-CH(Me)Et | 665 | 0.29 | 50 |
| Pr₂CHNHC(O) | NHCH₂CHEt₂ | 679 | 0.41 | 42 |
| MePr₂CNHC(O) | NHCH₂CMe₂Et | 693 | 0.36 | 29 |

TABLE IV-continued

Compounds of Formula 1 having the formula A—B—Tbg—CH$_2$—(R)-CH—(CH$_2$C(O)cMe3C(O)—Asp(cyPn)—E wherein A—B and E are designated as follows:

| A—B | E | FAB/MS (m/z) (M + H)$^+$ | IC$_{50}$ μM | EC$_{50}$ μM |
|---|---|---|---|---|
| Pr$_2$CHNHC(O) | NHNHCMe$_3$ | 666 | 0.22 | 84 |
| Me(CH$_2$=CHCH$_2$)$_2$—CNHC(O) | NHCH$_2$CMe$_3$ | 691 | 0.27 | 30 |
| MePr$_2$CNHC(O) | NHCH$_2$CMe$_3$ | 678 | 0.28 | 26 |
| Pr$_2$CHNHC(O) | NHCH$_2$—(cyclohexyl) | 691 | 0.36 | 47 |
| EtPr$_2$CNHC(O) | NHCH$_2$CMe$_3$ | 693 | | 16 |
| (CH$_2$=CHCH$_2$)$_2$—CHNHC(O) | NHCH$_2$CMe$_3$ | 661 | 0.37 | 100 |
| Bu$_2$CHNHC(O) | NHCH$_2$CMe$_3$ | 693 | 0.53 | 65 |
| Pr$_2$CHNHC(O) | NH—(S)-CH(CMe$_3$)CH$_2$OH | 695 | 0.23 | 48 |
| Me$_2$PrCNHC(O) | NHCH$_2$CMe$_3$ | 651 | 0.39 | 58 |
| Pr$_2$CHNHC(O) | NHCH$_2$CEt$_2$Me | 693 | 0.34 | 18 |
| Pr$_2$CHNHC(O) | NHCMe$_2$CMe$_3$ | 693 | 0.51 | 38 |
| (CH$_2$=CHCH$_2$)$_2$—CHNHC(O) | NH—(R)-CH(Me)CMe$_3$ | 675 | 0.32 | 48 |
| Pr$_2$CHNHC(O) | NH—(R)-CH(Me)C(Me)$_2$—Et | 693 | 0.50 | 21 |
| Pr$_2$CHNHC(O) | cis-NH—(2-methyl-cyclohexyl) | 691 | 0.67 | 75 |
| Pr$_2$CHNHC(O) | trans-NH—(2-methyl-cyclohexyl) | 691 | 0.69 | 60 |
| (R,S)-EtPrCH—NHC(O) | NHCH$_2$CMe$_3$ | 651 | 0.23 | 35 |
| (R,S)-EtBuCH—NHC(O) | NHCH$_2$CMe$_3$ | 665 | 0.26 | 35 |
| Pr$_2$CHNHC(O) | NH—(R)-CH(Et)CMe$_3$ | 693 | 0.34 | 10 |
| Pr$_2$CHNHC(O) | NH—(2,2-dimethyl-cyclohexyl) | 706 | 0.40 | 24 |
| EtPr$_2$CNHC(O) | NH—(R)-CH(Me)CMe$_3$ | 708 | 0.41 | 10 |
| Pr$_2$CHNHC(O) | NHCH$_2$CMe$_2$Pr | 694 | 0.42 | 35 |
| Pr$_2$CHNHC(O) | NH—(R)-CH(Me)CH$_2$CMe$_3$ | 694 | 0.37 | 14 |
| Pr$_2$CHNHC(O) | NHCH$_2$CH$_2$CMe$_3$ | 701* | 0.58 | 72 |
| Pr$_2$CHNHC(O) | NH—(R)-CH(Pr)CMe$_3$ | 707 | 0.43 | 15 |
| Pr$_2$CHNHC(O) | NH—(2,2-dimethyl-cyclopentyl) | 691 | 0.38 | 31 |
| Pr$_2$CHNHC(O) | NH—N(Me)CMe$_3$ | 680 | 0.27 | 110 |
| Pr$_2$CHNHC(O) | NHCH$_2$CEt$_3$ | 707 | 0.52 | 19 |
| EtPr$_2$CNHC(O) | NH—(R)-CH(Et)CMe$_3$ | 722 | 0.36 | 6 |
| Pr$_2$CHNHC(O) | NH—(R)-CH(Me)CHEt$_2$ | 693 | 0.33 | 16 |
| Pr$_2$CHNHC(O) | NHN(Et)CMe$_3$ | 694 | 0.22 | 80 |

*(M + Na)

TABLE V

| Compounds of Formula 1 | FAB/MS (m/z) (M + H)$^+$ | IC$_{50}$ μM | EC$_{50}$ μM |
|---|---|---|---|
| Pr$_2$CHNHC(O)—Tbg—CH$_2$—(R)-CH(CH$_2$—C(O)CHMe$_2$)C(O)—Asp(cyPn)—NHCH$_2$CMe$_3$ | 673* | 0.36 | 39 |
| Pr$_2$CHNHC(O)—Tbg—CH$_2$—(R)-CH—(CH$_2$C(O)CH$_2$CMe$_3$)C(CF)—Asp(cyPn)—Leu—OH | 679 | | 80 |
| Pr$_2$CHNHC(O)—Tbg—CH$_2$—(R)-CH{CH$_2$—C(O)—(cyclohexyl)}C(O)—Asp(cyPn)—NHCH$_2$CMe$_3$ | 691 | 0.37 | 61 |
| Pr$_2$CHNHC(O)—Tbg—CH$_2$—(R)-CH{CH$_2$—C(O)—(cyclobutyl)}C(O)—Asp(cyPn)—NHCH$_2$CMe$_3$ | 663 | 0.31 | 46 |
| Pr$_2$CHNHC(O)—Tbg—CH$_2$—(R)-CH(CH$_2$—C(O)CMe$_3$)C(O)—Asp{(R)-allyl}—NHCH$_2$CMe$_3$ | 651 | 0.30 | 62 |
| Pr$_2$CHNHC(O)—Tbg—CH$_2$—(R)-CH(CH$_2$—C(O)CMe$_3$)C(O)—Asp{(R)-Pr}—NHCH$_2$CMe$_3$ | 653 | 0.25 | 46 |
| Pr$_2$CHNHC(O)—Tbg—CH$_2$—(R)-CH(CH$_2$—C(O)CMe$_2$Et)C(O)—Asb(cyPn)—NHCH$_2$—CMe$_3$ | 679 | 0.21 | 33 |

| Compounds of Formula 1 | FAB/MS (m/z) (M + H)+ | IC$_{50}$ μM | EC$_{50}$ μM |
|---|---|---|---|
| Pr$_2$CHNHC(O)—Tbg—CH$_2$—(R)-CH{CH$_2$—C(O)—(1-methylcyclopentyl)}C(O)—Asp(cyPn)—NHCH$_2$CMe$_3$ | 691 | 0.24 | 35 |
| Pr$_2$CHNHC(O)—NH—(S)-CH(CMe$_2$Et)—C(O)—CH$_2$—(R)-CH(CH$_2$C(O)CMe$_3$)C(O)—Asp—(cyPn)—NH—(R)-CH(Me)CMe$_3$ | 693 | 0.25 | 13 |
| Pr$_2$CHNHC(O)—Val—CH$_2$—(R)-CH(CH$_2$—C(O)CMe$_3$)C(O)—Asp(cyPn)—NH—(R)-CH(Me)CMe$_3$ | 665 | 0.22 | 37 |

*(M + Na)

We claim:

1. A peptide of formula 1

Formula 1 wherein

A is phenylacetyl, phenylpropionyl, (4-aminophenyl)-propionyl, (4-fluorophenyl)propionyl, (4-hydroxyphenyl)propionyl, (4-methoxyphenyl)-propionyl, 2-(phenylmethyl)-3-phenylpropionyl, 2-{(4-fluorophenyl)methyl}-3-(4-fluorophenyl)propionyl, 2-{(4-methoxyphenyl)methyl}-3-(4-methoxyphenyl) propionyl or benzylaminocarbonyl;

B is (N-Me)-Val or (N-Me)-Ile;

or A and B together form a saturated or unsaturated alkylaminocarbonyl selected from the group of butylaminocarbonyl, 1-methylethylaminocarbonyl, 1-methylpropylaminocarbonyl, 1-ethylpropylaminocarbonyl, 1,1-dimethylbutylaminocarbonyl, 1-ethylbutylaminocarbonyl, 1-propylbutylaminocarbonyl, 1-ethylpentylaminocarbonyl, 1-butylpentylaminocarbonyl, 2-ethylbutylaminocarbonyl, 2-ethylpentylaminocarbonyl, 1-methyl-1-propylbutylamino-carbonyl, 1-ethyl-1-propylbutylaminocarbonyl, 1,1-dipropylbutylaminocarbonyl, (1-propylcyclopentyl)aminocarbonyl, (1-propylcyclohexyl)-aminocarbonyl, 1-(2-propenyl)-3-butenylaminocarbonyl, 1-methyl-1-(2-propenyl)-3-butenylaminocarbonyl and 1-ethyl-1-(2-propenyl)-3-butenylaminocarbonyl;

D is Val, Ile or Tbg;

R$^1$ is 1-methylethyl, 1,1-dimethylethyl, 1-methylpropyl, 1,1-dimethylpropyl, 2,2-dimethylpropyl, cyclobutyl, cyclopentyl, cyclohexyl, 1-methylcyclopentyl, NMe$_2$, NEt$_2$, pyrrolidino or morpholino;

R$^2$ is hydrogen,

R$^3$ is methyl, ethyl, 1-methylethyl, 1,1-dimethylethyl, propyl, 2-propenyl or benzyl, and the carbon atom bearing R$^2$ and R$^3$ has the (R)-configuration, or R$^2$ and R$^3$ each independently is methyl or ethyl, or R$^2$ and R$^3$ together with the carbon atom to which they are attached form a cyclobutyl, cyclopentyl or cyclohexyl; and E is NHR$^9$ wherein R$^9$ is 2-methylpropyl, 2,2-dimethylpropyl, 1(R),2,2trimethypropyl, 1,1,2,2-tetramethylpropyl, 1(R)-ethyl-2,2-dimethylpropyl, 2-(R,S)-methylbutyl, 2,2-dimethylbutyl, 3,3-dimethylbutyl, 1(R),2,2-trimethylbutyl, 1(R),3,3-trimethylbutyl, 2-ethylbutyl, 2,2-diethylbutyl, 2-ethyl-1(R)-methylbutyl, 2-ethyl-2methylbutyl, 1(R)-ethyl-3,3-dimethylbutyl, 2,2-dimethylpentyl, cis- or trans-2-methylcyclohexyl, 2,2-dimethylcyclohexyl or cyclohexylmethyl; or E is NHNR$^{10}$R$^{11}$ wherein R$^{10}$ is hydrogen, methyl or ethyl and R$^{11}$ is 1,1-dimethylethyl; or E is NHCH(R$^{12}$)—Z wherein the carbon atom bearing R$^{12}$ has the (S)-configuration, R$^{12}$ is 1,1-dimethylethyl, 1-methylpropyl, 2-methylpropyl, 2,2-dimethylpropyl or cyclohexylmethyl and Z is CH$_2$OH, C(O)OH, C(O)NH$_2$ or C(O)OR$^{13}$ wherein R$^{13}$ is methyl, ethyl or propyl;

or a pharmaceutically acceptable salt thereof.

2. A peptide as defined in claim 1 wherein A is phenylpropionyl, 2-(phenylmethyl)-3-phenylpropionyl or benzylaminocarbonyl; B is (N-Me)Val; D is Tbg; R$^1$ is 1-methylethyl, 1,1-dimethylethyl, 1-methylpropyl, 1,1-dimethylpropyl, 2,2-dimethylpropyl, cyclobutyl, cyclopentyl, cyclohexyl or 1-methylcyclopentyl; R$^2$ is hydrogen and R$^3$ is methyl, ethyl, 1-methylethyl, propyl or benzyl, and the carbon atom bearing R$^2$ and R$^3$ has the (R)-configuration, or R$^2$ and R$^3$ each independently is methyl or ethyl, or R$^2$ and R$^3$ together with the carbon atom to which they are attached form a cyclobutyl, cyclopentyl or cyclohexyl; and E is NHR$^9$ wherein R$^9$ is 2,2-dimethylpropyl, 1(R),2,2-trimethylpropyl, 1(R)-ethyl-2,2-dimethylpropyl, 2,2-dimethylbutyl or 1(R)-ethyl-3,3-dimethylbutyl, or E is NHCH(R$^{12}$)—Z wherein the carbon atom bearing R$^{12}$ has the (S)-configuration, R$^{12}$ is 2,2-dimethylpropyl and Z is CH$_2$OH, C(O)OH, C(O)NH$_2$ or C(O)OR$^{13}$ wherein R$^{13}$ is methyl, ethyl or propyl; or a pharmaceutically acceptable salt thereof.

3. A peptide as defined in claim 1 wherein A and B together form a saturated or unsaturated alkylaminocarbonyl selected from the group of 1-ethylpropylaminocarbonyl, 1-ethylbutylaminocarbonyl, 1-propylbutylaminocarbonyl, 2-ethylpentylaminocarbonyl, 1-methyl-1-propylbutylaminocarbonyl, 1-ethyl-1-propylaminocarbonyl, 1,1-dipropylbutylaminocarbonyl, (1-propylcyclopentyl)aminocarbonyl, 1-(2-propenyl)-3-butenylaminocarbonyl and 1-ethyl-1-(2-propenyl)-3-butenylaminocarbonyl; D is Tbg; R$^1$ is 1-methylethyl, 1,1-dimethylethyl, 1-methylpropyl, 1,1-dimethylpropyl, 2,2-dimethylpropyl, cyclobutyl, cyclopentyl, cyclohexyl or 1-methylcyclopentyl; R$^2$ is hydrogen and R$^3$ is methyl, ethyl, 1-methylethyl, propyl or benzyl, and the carbon atom bearing R$^2$ and R$^3$ has the (R)-configuration, or R$^2$ and R$^3$ each independently is methyl or ethyl, or R$^2$ and R$^3$ together with the carbon atom to which they are attached form a cyclobutyl, cyclopentyl or cyclohexyl; and E is NHR$^9$ wherein R$^9$ is 2,2-dimethylpropyl, 1(R), 2,2-trimethylpropyl, 1(R)-ethyl-2,2-dimethylpropyl, 2,2-dimethylbutyl or 1(R)-ethyl-3,3-dimethylbutyl, or E is NHCH(R$^{12}$)—Z wherein the carbon atom bearing R$^{12}$ has the (S)-configuration R$^{12}$ is 2,2-dimethylpropyl and Z is CH$_2$OH, C(O)OH, C(O)NH$_2$ or C(O)OR$^{13}$ wherein R$^{13}$ is methyl, ethyl or propyl; or a pharmaceutically acceptable salt thereof.

4. A peptide as defined in claim 1 selected from the group consisting of:

PhCH$_2$CH$_2$C(O)—(N-Me)Val-Tbg-CH$_2$—(R)—CH(CH$_2$C(O)CMe$_3$)C(O)-Asp(cyPn)-γMeLeucinol, PhCH$_2$CH$_2$C(O)—(N-Me)Val-Tbg-CH$_2$—(R)—CH(CH$_2$C(O)CMe$_3$)C(O)-Asp(cyPn)-γMeLeu-OH, PhCH$_2$CH$_2$C(O)—(N-Me)Val-Tbg-CH$_2$—(R)—CH(CH$_2$C(O)CMe$_3$)C(O)-Asp(cyPn)-γMeLeu-NH$_2$, PhCH$_2$CH$_2$C(O)—(N—Me)Val-Tbg-CH$_2$—(R)—CH(CH$_2$C(O)CMe$_3$)C(O)-Asp(cyPn)-NHCH$_2$CMe$_3$, PhCH$_2$CH$_2$C(O)—(N-Me)Val-Tbg-CH$_2$—(R)—CH{CH$_2$C(O)-(cyclopentyl)}C(O)-Asp-(cyPn)-NHCH$_2$CMe$_3$, PhCH$_2$CH$_2$C(O)—(N—Me)Val-Tbg-CH$_2$—(S)—CH(CH$_2$C(O)CMe$_3$)C(O)-Asp{(R)-Me}-NHCH$_2$CMe$_3$, Et$_2$CHNHC(O)-Tbg-CH$_2$—(R)—CH(CH$_2$C(O)CMe$_3$)C(O)-Asp(cyPn)-NHCH$_2$CMe$_3$, Et$_2$CHNHC(O)-Tbg-CH$_2$—(R)—CH{CH$_2$C(O)-(pyrrolidino)}-C(O)-Asp(cyPn)-γMeLeucinol, Et$_2$CHNHC(O)-Tbg-CH$_2$—(R)—CH(CH$_2$C(O)CMe$_3$)C(O)-Asp(cyPn)-γMeLeu-OH, Et$_2$CHNHC(O)-Tbg-CH$_2$—(R)—CH(CH$_2$C(O)CMe$_3$)C(O)-Asp(cyPn)-γMeLeu-NH$_2$, Et$_2$CHNHC(O)-Tbg-CH$_2$—(R)—CH(CH$_2$C(O)CMe$_3$)CO-Asp(cyPn)-γMeLeucinol, Et$_2$CHNHC(O)-Tbg-CH$_2$—(R)—CH{CH$_2$C(O)-(cyclopentyl)}-C(O)-Asp(cyPn)-NHCH$_2$CMe$_3$, Et$_2$CHNHC(O)-Tbg-CH$_2$—(R)—CH(CH$_2$C(O)CMe$_3$)C(O)-Asp{(R)—Me}-NHCH$_2$CMe$_3$, Pr$_2$CHNHC(O)-Tbg-CH$_2$—(R)—CH(CH$_2$C(O)CMe$_3$)C(O)-Asp(cyPn)-γMeLeu-OH, Pr$_2$CHNHC(O)-Tbg-CH$_2$—(R)—CH(CH$_2$C(O)CMe$_3$)C(O)-Asp(cyPn)-γMeLeucinol, Pr$_2$CHNHC(O)-Tbg-CH$_2$—(R)—CH(CH$_2$C(O)CMe$_3$)C(O)-Asp(cyPn)-NHCH$_2$CMe$_3$, (1-propylcyclopentyl)aminocarbonyl-Tbg-CH$_2$—(R)—CH(CH$_2$C(O)CMe$_3$)C(O)-Asp(cyPn)-NHCH$_2$CMe$_3$, Pr$_2$CHNHC(O)-Tbg-CH$_2$—(R)—CH{CH$_2$C(O)-(cyclopentyl)}C(O)-Asp(cyPn)-NHCH$_2$CMe$_3$, Pr$_2$CHNHC(O)-Tbg-CH$_2$—(R)—CH(CH$_2$C(O)CMe$_3$)C(O)-Asp(cyPn)—NH—(R)—CH(Me)CMe$_3$, Pr$_2$CHNHC(O)-Tbg-CH$_2$—(R)—CH(CH$_2$C(O)CMe$_3$)C(O)-Asp(cyPn)-NHCH$_2$CMe$_2$Et, Pr$_2$CHNHC(O)-Tbg-CH$_2$—(R)—CH(CH$_2$C(O)CMe$_3$)C(O)-Asp(cyPn)-NHCH$_2$-(R,S)-CH(Me)Et, Pr$_2$CHNHC(O)-Tbg-CH$_2$—(R)—CH(CH$_2$C(O)CMe$_3$)C(O)-Asp(cyPn)-NHCH$_2$CHEt$_2$, MePr$_2$CNHC(O)-Tbg-CH$_2$—(R)—CH(CH$_2$C(O)CMe$_3$)C(O)-Asp(cyPn)-NHCH$_2$CMe$_2$Et, Pr$_2$CHNHC(O)-Tbg-CH$_2$—(R)—CH(CH$_2$C(O)CMe$_3$)C(O)-Asp(cyPn)-NHNHCMe$_3$, Me(CH$_2$=CHCH$_2$)$_2$—CNHC(O)-Tbg-CH$_2$—(R)—CH(CH$_2$C(O)CMe$_3$)C(O)-Asp(cyPn)-NHCH$_2$CMe$_3$, MePr$_2$CNHC(O)-Tbg-CH$_2$—(R)—CH(CH$_2$C(O)CMe$_3$)C(O)-Asp(cyPn)-NHCH$_2$CMe$_3$, Pr$_2$CHNHC(O)-Tbg-CH$_2$—(R)—CH(CH$_2$C(O)CMe$_3$)C(O)-Asp(cyPn)-NHCH$_2$-(cyclohexyl), EtPr$_2$CNHC(O)-Tbg-CH$_2$—(R)—CH(CH$_2$C(O)CMe$_3$)C(O)-Asp(cyPn)-NHCH$_2$CMe$_3$, (CH$_2$=CHCH$_2$)$_2$—CHNHC(O)-Tbg-CH$_2$—(R)—CH(CH$_2$C(O)CMe$_3$)C(O)-Asp(cyPn)-NHCH$_2$CMe$_3$, Bu$_2$CHNHC(O)-Tbg-CH$_2$—(R)—CH(CH$_2$C(O)CMe$_3$)C(O)-Asp(cyPn)-NHCH$_2$CMe$_3$, Pr$_2$CHNHC(O)-Tbg-CH$_2$—(R)—CH(CH$_2$C(O)CMe$_3$)C(O)-Asp(cyPn)-NH—(S)—CH(CMe$_3$)CH$_2$OH, Me$_2$PrCNHC(O)-Tbg-CH$_2$—(R)—CH(CH$_2$C(O)CMe$_3$)C(O)-Asp(cyPn)-NHCH$_2$CMe$_3$, Pr$_2$CHNHC(O)-Tbg-CH$_2$—(R)—CH(CH$_2$C(O)CMe$_3$)C(O)-Asp(cyPn)-NHCH$_2$CEt$_2$Me, Pr$_2$CHNHC(O)-Tbg-CH$_2$—(R)—CH(CH$_2$C(O)CMe$_3$)C(O)-Asp(cyPn)-NHCMe$_2$CMe$_3$, (CH$_2$=CHCH$_2$)$_2$—CHNHC(O)-Tbg-CH$_2$—(R)—CH(CH$_2$C(O)CMe$_3$)C(O)-Asp(cyPn)-NH—(R)—CH(Me)CMe$_3$, Pr$_2$CHNHC(O)-Tbg-CH$_2$—(R)—CH(CH$_2$C(O)CMe$_3$)C(O)-Asp(cyPn)-NH—(R)—CH(Me)C(Me)$_2$Et, Pr$_2$CHNHC(O)-Tbg-CH$_2$—(R)—CH(CH$_2$C(O)CMe$_3$)C(O)-Asp(cyPn)-cis-NH-(2-methylcyclohexyl), Pr$_2$CHNHC(O)-Tbg-CH$_2$—(R)—CH(CH$_2$C(O)CMe$_3$)C(O)-Asp(cyPn)-trans-NH-(2-methylcyclohexyl), (R,S)-EtPrCH-NHC(O)-Tbg-CH$_2$—(R)—CH(CH$_2$C(O)CMe$_3$)C(O)-Asp(cyPn)-NHCH$_2$CMe$_3$, (R,S)-EtBuCH-NHC(O)-Tbg-CH$_2$—(R)—CH(CH$_2$C(O)CMe$_3$)C(O)-Asp(cyPn)-NHCH$_2$CMe$_3$, Pr$_2$CHNHC(O)-Tbg-CH$_2$—(R)—CH(CH$_2$C(O)CMe$_3$)C(O)-Asp(cyPn)-NH—(R)—CH(Et)CMe$_3$, Pr$_2$CHNHC(O)-Tbg-CH$_2$—(R)—CH(CH$_2$C(O)CMe$_3$)C(O)-Asp(cyPn)-NH-(2,2-dimethylcyclohexyl), EtPr$_2$CNHC(O)-Tbg-CH$_2$—(R)—CH(CH$_2$C(O)CMe$_3$)C(O)-Asp(cyPn)-NH—(R)—CH(Me)CMe$_3$, Pr$_2$CHNHC(O)-Tbg-CH$_2$—(R)—CH(CH$_2$C(O)CMe$_3$)C(O)-Asp(cyPn)-NHCH$_2$CMe$_2$Pr, Pr$_2$CHNHC(O)-Tbg-CH$_2$—(R)—CH(CH$_2$C(O)CMe$_3$)C(O)-Asp(cyPn)-NH—(R)—CH(Me)CH$_2$CMe$_3$, Pr$_2$CHNHC(O)-Tbg-CH$_2$—(R)—CH(CH$_2$C(O)CMe$_3$)C(O)-Asp(cyPn)-NHCH$_2$CH$_2$CMe$_3$, Pr$_2$CHNHC(O)-Tbg-CH$_2$—(R)—CH(CH$_2$C(O)CMe$_3$)C(O)-Asp(cyPn)-NH—(R)—CH(Pr)CMe$_3$, Pr$_2$CHNHC(O)-Tbg-CH$_2$—(R)—CH(CH$_2$C(O)CMe$_3$)C(O)-Asp(cyPn)-NH-(2,2-dimethylcyclopentyl), Pr$_2$CHNHC(O)-Tbg-CH$_2$—(R)—CH(CH$_2$C(O)CMe$_3$)C(O)-Asp(cyPn)-NH—N(Me)CMe$_3$, Pr$_2$CHNHC(O)-Tbg-CH$_2$—(R)—CH(CH$_2$C(O)CMe$_3$)C(O)-Asp(cyPn)-NHCH$_2$CEt$_3$, EtPr$_2$CNHC(O)-Tbg-CH$_2$—(R)—CH(CH$_2$C(O)CMe$_3$)C(O)-Asp(cyPn)-NH—(R)—CH(Et)CMe$_3$, Pr$_2$CHNHC(O)-Tbg-CH$_2$—(R)—
CH(CH$_2$C(O)CMe$_3$)C(O)-Asp(cyPn)-NH—(R)—
CH(Me)CHEt$_3$, Pr$_2$CHNHC(O)-Tbg-CH$_2$—(R)—
CH(CH$_2$C(O)CMe$_3$)C(O)-Asp(cyPn)-NHN(Et)CMe$_3$, Pr$_2$CHNHC(O)-Tbg-CH$_2$—(R)—
CH(CH$_2$C(O)CHMe$_3$)C(O)-Asp(cyPn)-NHCH$_2$CMe$_3$, Pr$_2$CHNHC(O)-Tbg-CH$_2$—(R)—
CH(CH$_2$C(O)CH$_2$CMe$_3$)C(O)-Asp(cyPn)-Leu-OH, Pr$_2$CHNHC(O)-Tbg-CH$_2$—(R)—CH{CH$_2$C(O)-(cyclohexyl)}-C(O)-Asp(cyPn)-NHCH$_2$CMe$_3$, Pr$_2$CHNHC(O)-Tbg-CH$_2$—(R)—CH{CH$_2$C(O)-(cyclobutyl)}-C(O)-Asp(cyPn)-NHCH$_2$CMe$_3$, Pr$_2$CHNHC(O)-Tbg-CH$_2$—(R)—
CH(CH$_2$C(O)CMe$_3$)C(O)-Asp{(R)-allyl}-NHCH$_2$CMe$_3$, Pr$_2$CHNHC(O)-Tbg-CH$_2$—(R)—
CH(CH$_2$C(O)CMe$_3$)C(O)-Asp{(R)-Pr}-NHCH$_2$CMe$_3$, Pr$_2$CHNHC(O)-Tbg-CH$_2$—(R)—
CH(CH$_2$C(O)CMe$_2$Et)C(O)-Asp(cyPn)-NHCH$_2$CMe$_3$, Pr$_2$CHNHC(O)-Tbg-CH$_2$—(R)—CH{CH$_2$C (O)-(1-methylcyclopentyl)}C(O)-Asp(cyPn)-NHCH$_2$CMe$_3$, Pr$_2$CHNHC(O)—NH—(S)—CH(CMe$_2$Et)-C(O)—
CH$_2$—(R)—CH(CH$_2$C(O)CMe$_3$)C(O)-Asp(cyPn)-NH—(R)—CH(Me)CMe$_3$, and Pr$_2$CHNHC(O)-Val-CH$_2$—(R)—
CH(CH$_2$C(O)CMe$_3$)C(O)-Asp(cyPn)-NH—(R)—
CH(Me)CMe$_3$.

5. A pharmaceutical composition comprising an antiherpes virally effective amount of a peptide as defined in claim 1, or a pharmaceutically acceptable salt thereof, and a pharmaceutically or veterinarily acceptable carrier.

6. A cosmetic composition comprising a peptide as defined in claim 1, or a pharmaceutically acceptable salt thereof, and a physiologically acceptable carrier suitable for topical application.

7. A method of treating a herpes viral infection in a mammal comprising administering to the mammal an antiherpes virally effective amount of the peptide as defined in claim 1, or a pharmaceutically acceptable salt thereof.

8. A method of inhibiting the replication of herpes virus by contacting the virus with a herpes viral ribonucleotide reductase inhibiting amount of the peptide as defined in claim 1, or a pharmaceutically acceptable salt thereof.

9. A method of treating herpes viral infections in a mammal comprising administering thereto an effective amount of a combination of an antiviral nucleoside analog selected from the group of acyclovir, 6-deoxyacyclovir, 2,6-diamino-9-{(2-hydroxyethoxy)methyl}-purine vidarabine, idoxuridine, trifluridine, ganciclovir, edoxudine, brovavir, fiacitabine, penciclovir, famciclovir and rociclovir and a ribonucleotide reductase inhibiting peptide, or a pharmaceutically acceptable salt thereof, as recited in claim 1.

10. The method of claim 9 wherein the nucleoside analog and the peptide are administered sequentially or simultaneously.

11. The method of claim 9 where the combination is administered topically.

12. A method of treating herpes simplex virus type 1, or type 2, infections in a mammal comprising administering thereto an effective amount of a pharmaceutical composition as recited in claim 8 wherein the peptide of formula 1 of the composition is selected from the group consisting of:

PhCH$_2$CH$_2$C(O)-(N-Me)Val-Tbg-CH$_2$—(R)—
CH(CH$_2$C(O)CMe$_3$)C(O)-Asp(cyPn)-γMeLeucinol, Pr$_2$CHNHC(O)-Tbg-CH$_2$—(R)—
CH(CH$_2$C(O)CMe$_3$)C(O)-Asp(cyPn)-γMeLeu-OH, Pr$_2$CHNHC(O)-Tbg-CH$_2$—(R)—
CH(CH$_2$C(O)CMe$_3$)C(O)-Asp(cyPn)-γMeLeucinol, Pr$_2$CHNHC(O)-Tbg-CH$_2$—(R)—
CH(CH$_2$C(O)CMe$_3$)C(O)-Asp(cyPn)-NH$_2$CH$_2$CMe$_3$, (1-propylcyclopentyl)aminocarbonyl-Tbg-CH$_2$—(R)—
CH(CH$_2$C(O)CMe$_3$)C(O)-Asp(cyPn)-NHCH$_2$CMe$_3$, Pr$_2$CHNHC(O)-Tbg-CH$_2$—(R)—CH{CH$_2$C(O)-(cyclopentyl)}-C(O)-Asp(cyPn)-NHCH$_2$CMe$_3$, Pr$_2$CHNHC(O)-Tbg-CH$_2$—(R)—
CH(CH$_2$C(O)CMe$_3$)C(O)-Asp(cyPn)-NH—(R)—
CH(Me)CMe$_3$, Pr$_2$CHNHC(O)-Tbg-CH$_2$—(R)—
CH(CH$_2$C(O)CMe$_3$)C(O)-Asp(cyPn)-NHCH$_2$CMe$_2$Et, EtPr$_2$CHNC(O)-Tbg-CH$_2$—(R)—
CH(CH$_2$C(O)CMe$_3$)C(O)-Asp(cyPn)-NHCH$_2$CMe$_3$, Pr$_2$CHNHC(O)-Tbg-CH$_2$—(R)—
CH(CH$_2$C(O)CMe$_3$)C(O)-Asp(cyPn)-NHCH$_2$CEt$_2$Me, Pr$_2$CHNHC(O)-Tbg-CH$_2$—(R)—
CH(CH$_2$C(O)CMe$_3$)C(O)-Asp(cyPn)-NH—(R)—
CH(Et)CMe$_3$, EtPr$_2$CNHC(O)-Tbg-CH$_2$—(R)—
CH(CH$_2$C(O)CMe$_3$)C(O)-Asp(cyPn)-NH—(R)—
CH(Me)CMe$_3$, Pr$_2$CHNHC(O)-Tbg-CH$_2$—(R)—
CH(CH$_2$C(O)CMe$_3$)C(O)-Asp(cyPn)-NH—(R)—
CH(Me)CH$_2$CMe$_3$, Pr$_2$CHNHC(O)-Tbg-CH$_2$—(R)—
CH(CH$_2$C(O)CMe$_3$)C(O)-Asp(cyPn)-NH—(R)—
CH(Pr)CMe$_3$, Pr$_2$CHNHC(O)-Tbg-CH$_2$—(R)—
CH(CH$_2$C(O)CMe$_3$)C(O)-Asp(cyPn)-NHCH$_2$CEt$_3$, EtPr$_2$CNHC(O)-Tbg-CH$_2$—(R)—
CH(CH$_2$C(O)CMe$_3$)C(O)-Asp(cyPn)-NH—(R)—
CH(Et)CMe$_3$, Pr$_2$CHNHC(O)-Tbg-CH$_2$—(R)—
CH(CH$_2$C(O)CMe$_3$)C(O)-Asp(cyPn)-NH—(R)—
CH(Me)CHEt$_2$, and Pr$_2$CHNHC(O)-NH—(S)—CH(CMe$_2$Et)C(O)-CH$_2$—
(R)—CH(CH$_2$C(O)CMe3)C(O)Asp(cyPn)-NH—
(R)—CH(Me)CMe$_3$.

13. A pharmaceutical composition comprising a ribonucleotide reductase inhibiting peptide, or a pharmaceutically acceptable salt thereof, as recited in claim 1, an antiviral nucleoside analog selected from the group of acyclovir, 6-deoxyacyclovir, 2,6-diamino-9-{(2-hydroxyethoxy)methyl}purine, vidarabine, idoxuridine, trifluridine, ganciclovir, edoxudine, brovavir, fiacitabine, penciclovir, famciclovir and rociclovir, or a pharmaceutically acceptable salt thereof, and a pharmaceutically or veterinarily acceptable carrier.

14. A process for preparing a peptide as defined in claim 1, or a therapeutically acceptable salt thereof, comprising:
   a) stepwise coupling, in the order of the sequence of the peptide, of the amino acid or derived amino acid residues, and non-peptidic fragments of the peptide, in which
      i) reactive side chain groups of the residue or fragments are protected with suitable protective groups to prevent chemical reactions from occurring at that site until the protective group is ultimately removed after the completion of the stepwise coupling;

ii) an α-amino group of a coupling reactant is protected by an α-amino protective group while the free carboxy group of that reactant couples with the free α-amino group of the second reactant; the α-amino protective group being one which can be selectively removed to allow the subsequent coupling step to take place at that α-amino group; and iii) the C-terminal carboxyl of the amino acid residue of the amino acid residue or peptide fragment, which is to become the C-terminal function of the protected peptide, if present, is protected with a suitable protective group which will prevent chemical reaction occurring at that site until after the desired amino acid sequence for the peptide has been assembled; and b) at the completion of the coupling, eliminating any protecting groups and, if required, effecting standard transformations to obtain the peptide of claim 1; and if desired, converting the peptide into a pharmaceutically acceptable salt.

* * * * *